US012751755B2

(12) United States Patent
Doyle

(10) Patent No.: US 12,751,755 B2
(45) Date of Patent: Oct. 6, 2026

(54) IMPACTOR

(71) Applicant: Smith & Nephew, Inc., Memphis, TN (US)

(72) Inventor: Ruben Doyle, Bramley (GB)

(73) Assignee: Smith & Nephew, Inc., Memphis, TN (US)

( * ) Notice: Subject to any disclaimer, the term of this patent is extended or adjusted under 35 U.S.C. 154(b) by 104 days.

(21) Appl. No.: 18/396,789

(22) Filed: Dec. 27, 2023

(65) Prior Publication Data

US 2024/0130771 A1 Apr. 25, 2024

Related U.S. Application Data

(63) Continuation of application No. 18/193,116, filed on Mar. 30, 2023, now Pat. No. 11,918,268, which is a (Continued)

(30) Foreign Application Priority Data

Oct. 9, 2020 (GB) .................................. 2016060.2
Jul. 15, 2021 (GB) .................................. 2110224.9

(51) Int. Cl.

| | |
|---|---|
| ***A61B 17/92*** | (2006.01) |
| ***A61F 2/46*** | (2006.01) |
| ***B25D 11/06*** | (2006.01) |
| *A61B 17/00* | (2006.01) |
| *A61B 17/56* | (2006.01) |

(52) U.S. Cl.

CPC ............ *A61B 17/92* (2013.01); *B25D 11/064* (2013.01); *A61B 2017/00876* (2013.01); *A61B 2017/564* (2013.01); *A61B 2017/924* (2013.01); *A61B 2017/927* (2013.01); (Continued)

(58) Field of Classification Search

CPC . A61B 17/92–2017/928; B25D 11/064; A61F 2002/4681

See application file for complete search history.

(56) References Cited

U.S. PATENT DOCUMENTS 85,926 A 1/1869 Grover
852,926 A * 5/1907 Carver ................. B25D 11/064 173/117

(Continued)

FOREIGN PATENT DOCUMENTS

CN 2423872 A1 3/2001
CN 2423872 Y 3/2001

(Continued)

OTHER PUBLICATIONS

Office Action for Application No. GB2016060.2, mailed Sep. 6, 2021, 3 pages.

(Continued)

*Primary Examiner* — David W Bates
(74) *Attorney, Agent, or Firm* — KDW Firm PLLC

(57) ABSTRACT

There is disclosed an orthopaedic impactor, comprising: a strike assembly arranged to impart a force to an object; and a winding arranged to receive a current and thereby generate a magnetic field. The winding is arranged to interact with the strike assembly so that, in use, a magnetic field generated by the winding causes the strike assembly to move so as to impart the force to the object.

20 Claims, 13 Drawing Sheets

Related U.S. Application Data continuation of application No. PCT/GB2021/052604, filed on Oct. 7, 2021.

(52) U.S. Cl.
CPC ................. *A61F 2002/4681* (2013.01); *A61F 2002/4698* (2013.01); *B25D 2250/145* (2013.01); *B25D 2250/335* (2013.01)

(56) References Cited

U.S. PATENT DOCUMENTS 864,259 A * 8/1907 Rathbun .............. B25D 11/064 173/117
1,511,566 A 10/1924 Kollock
1,578,275 A 3/1926 Johnston
1,609,494 A 12/1926 Payne
1,637,192 A 7/1927 Jimerson
1,777,875 A 10/1930 Champayne
1,809,884 A 6/1931 Anthony
1,825,072 A 9/1931 Charles
1,837,197 A * 12/1931 Berman ................. H02K 33/12 310/16
2,542,695 A * 2/1951 Neff ....................... A61B 17/92 D24/142
2,655,921 A * 10/1953 Haboush ............ A61B 17/1604 81/463
2,713,992 A 7/1955 Snyder
2,749,548 A 6/1956 Turner
2,967,302 A 1/1961 Loveless
3,149,681 A 9/1964 Drew
3,430,707 A 3/1969 Rees
3,891,036 A 6/1975 Schmidt
4,215,297 A * 7/1980 Jacquemet ........... B25D 11/064 318/132
4,428,439 A 1/1984 Moreno
4,450,919 A 5/1984 Cousineau
4,468,594 A * 8/1984 Jacquemet .............. E02D 11/00 318/128
4,489,792 A 12/1984 Fahim
4,727,875 A 3/1988 Dory
5,057,112 A 10/1991 Sherman
5,098,430 A 3/1992 Fleenor
5,108,400 A 4/1992 Appel et al.
5,352,230 A 10/1994 Hood
5,485,887 A * 1/1996 Mandanis .............. B25D 17/06 173/91
5,494,115 A 2/1996 Hwong
6,138,772 A 10/2000 Miescher
6,264,661 B1 * 7/2001 Jerger ................ A61B 17/1697 606/100
6,723,102 B2 4/2004 Johnson
6,868,918 B2 3/2005 Shinohara
6,991,655 B2 1/2006 Iversen
7,189,241 B2 3/2007 Yoon
7,594,933 B2 9/2009 Kammerzell
7,604,637 B2 10/2009 Johnson
7,634,306 B2 12/2009 Sarin
7,636,595 B2 12/2009 Marquart
7,637,327 B2 12/2009 Grunig
7,780,681 B2 8/2010 Sarin
7,927,338 B2 4/2011 Laffargue
8,007,448 B2 8/2011 Moctezuma De La Barrera
8,206,405 B2 6/2012 Beverland
8,393,409 B2 3/2013 Pedicini
8,394,036 B2 3/2013 Kozak
8,449,551 B2 5/2013 Amiot
8,494,825 B2 7/2013 Thornberry
8,602,124 B2 12/2013 Pedicini
8,695,726 B2 4/2014 Pedicini
8,709,016 B2 4/2014 Park
8,731,253 B2 5/2014 Dardenne
8,790,351 B2 7/2014 Paradis
8,814,877 B2 8/2014 Wasielewski
8,828,008 B2 9/2014 Stubbs
8,861,818 B2 10/2014 Ito
8,936,105 B2 1/2015 Pedicini
8,936,106 B2 1/2015 Pedicini
8,974,468 B2 3/2015 Borja
8,979,859 B2 3/2015 Leparmentier
9,005,213 B2 4/2015 Fortin
9,011,456 B2 4/2015 Ranawat
9,017,335 B2 4/2015 Stiehl
9,044,345 B2 6/2015 Warkentine
9,095,375 B2 8/2015 Haimerl
9,168,153 B2 10/2015 Bettenga
9,168,154 B2 10/2015 Behzadi
9,220,572 B2 12/2015 Meridew
9,220,612 B2 12/2015 Behzadi
9,248,002 B2 2/2016 McCarthy
9,308,005 B2 4/2016 Fitz
9,375,222 B2 6/2016 Fitz
9,402,727 B2 8/2016 Stubbs
9,408,617 B2 8/2016 Ranawat
9,445,920 B2 9/2016 Baynham
9,469,160 B2 10/2016 Koshio
9,532,730 B2 1/2017 Wasielewski
9,539,112 B2 1/2017 Thornberry
9,554,863 B2 1/2017 Paradis
9,572,682 B2 2/2017 Aghazadeh
9,585,768 B2 3/2017 Sherman
9,649,160 B2 5/2017 van der Walt
9,649,201 B2 5/2017 Stuchin
9,649,202 B2 5/2017 Behzadi
9,662,228 B2 5/2017 McCarthy
9,713,506 B2 7/2017 Fanson
9,713,539 B2 7/2017 Haimerl
9,763,738 B2 9/2017 Paradis
9,827,112 B2 11/2017 Bettenga
9,901,354 B2 2/2018 Pedicini
9,931,059 B2 4/2018 Borja
9,941,779 B2 4/2018 Paine et al.
9,949,797 B2 4/2018 Meridew
9,980,780 B2 5/2018 Lang
9,987,148 B2 6/2018 Li
RE46,954 E 7/2018 Pedicini
RE46,979 E 8/2018 Pedicini
10,149,711 B2 12/2018 Bittenson
10,159,530 B2 12/2018 Lang
10,166,083 B2 1/2019 Paradis
10,172,722 B2 1/2019 Behzadi
10,245,162 B2 4/2019 Behzadi
10,271,963 B2 4/2019 Lye
10,321,852 B2 6/2019 Borja
10,342,591 B2 7/2019 Pedicini
10,363,149 B2 7/2019 van der Walt
10,405,928 B2 9/2019 Falardeau
10,413,425 B2 9/2019 Behzadi
10,420,567 B2 9/2019 Pedicini
10,426,540 B2 10/2019 Behzadi
10,441,244 B2 10/2019 Behzadi
10,456,271 B2 10/2019 Behzadi
10,463,415 B2 11/2019 Walter
10,463,505 B2 11/2019 Behzadi
10,463,507 B2 11/2019 Nic
10,470,897 B2 11/2019 Behzadi
10,478,318 B2 11/2019 Behzadi
10,568,643 B2 * 2/2020 Johnson ............... A61B 17/164
10,603,050 B2 * 3/2020 Pedicini ............... B25D 11/066
10,603,115 B2 3/2020 van der Walt
RE47,963 E 4/2020 Pedicini
RE47,997 E 5/2020 Pedicini
10,716,630 B2 7/2020 Krebs
10,743,950 B2 8/2020 Nikou
RE48,184 E 9/2020 Pedicini
RE48,251 E 10/2020 Pedicini
10,792,799 B2 10/2020 Binder et al.
RE48,387 E 1/2021 Pedicini
RE48,388 E 1/2021 Pedicini
10,881,470 B2 1/2021 Falardeau
10,894,311 B2 1/2021 Yamashita
10,912,597 B2 2/2021 Pedicini
10,918,499 B2 2/2021 Nielsen
10,980,645 B2 4/2021 Falardeau

(56) References Cited

U.S. PATENT DOCUMENTS

| | | | |
|---|---|---|---|
| 11,013,503 B2 | 5/2021 | Pedicini | |
| 11,020,245 B2 | 6/2021 | van der Walt | |
| 11,033,315 B2 | 6/2021 | Pedicini | |
| 11,076,867 B2 | 8/2021 | Pedicini | |
| 11,076,903 B2 | 8/2021 | Pedicini | |
| 11,083,512 B2 | 8/2021 | Pedicini | |
| 11,090,170 B2 | 8/2021 | Li | |
| 11,103,363 B2 | 8/2021 | Bettenga | |
| 11,134,962 B2 | 10/2021 | Pedicini | |
| 11,147,638 B2 | 10/2021 | Nikou | |
| 11,179,062 B2 | 11/2021 | Borja | |
| 11,213,336 B2 | 1/2022 | Walter | |
| 11,229,491 B2 | 1/2022 | Nikou | |
| 11,234,775 B2 | 2/2022 | Shiels | |
| 11,284,951 B2 | 3/2022 | Nikou | |
| 11,918,268 B2 * | 3/2024 | Doyle | A61B 17/92 |
| 12,193,718 B2 * | 1/2025 | Lyon | A61B 17/92 |
| 2004/0087852 A1 | 5/2004 | Chen | |
| 2004/0147926 A1 | 7/2004 | Iversen | |
| 2004/0206525 A1 | 10/2004 | Rask | |
| 2005/0065617 A1 | 3/2005 | Moctezuma de la Barrera | |
| 2005/0148855 A1 | 7/2005 | Kienzle | |
| 2005/0187562 A1 | 8/2005 | Grimm | |
| 2006/0064109 A1 | 3/2006 | Iversen | |
| 2006/0094958 A1 | 5/2006 | Marquart | |
| 2006/0190011 A1 | 8/2006 | Ries | |
| 2007/0222401 A1 | 9/2007 | Trumper et al. | |
| 2007/0225725 A1 | 9/2007 | Heavener | |
| 2008/0269596 A1 | 10/2008 | Revie | |
| 2010/0076505 A1 | 3/2010 | Borja | |
| 2010/0137871 A1 | 6/2010 | Borja | |
| 2010/0204685 A1 | 8/2010 | Ippisch | |
| 2010/0206593 A1 | 8/2010 | Schad et al. | |
| 2010/0261998 A1 | 10/2010 | Stiehl | |
| 2010/0274253 A1 | 10/2010 | Ure | |
| 2011/0190775 A1 | 8/2011 | Ure | |
| 2012/0209117 A1 | 8/2012 | Mozes | |
| 2012/0209419 A1 | 8/2012 | Kang | |
| 2012/0215267 A1 | 8/2012 | Pedicini | |
| 2012/0283599 A1 | 11/2012 | Borja | |
| 2012/0323247 A1 | 12/2012 | Bettenga | |
| 2013/0161039 A1 | 6/2013 | Rakaczki et al. | |
| 2013/0161050 A1 | 6/2013 | Pedicini | |
| 2013/0172907 A1 | 7/2013 | Harris | |
| 2013/0261681 A1 * | 10/2013 | Bittenson | A61B 17/92<br>606/86 R |
| 2013/0333904 A1 | 12/2013 | Raggl et al. | |
| 2014/0052149 A1 | 2/2014 | van der Walt | |
| 2014/0135773 A1 | 5/2014 | Stein | |
| 2014/0135791 A1 | 5/2014 | Nikou | |
| 2014/0303631 A1 | 10/2014 | Thornberry | |
| 2014/0318823 A1 | 10/2014 | Pedicini | |
| 2014/0364848 A1 | 12/2014 | Heimbecher | |
| 2015/0142372 A1 | 5/2015 | Singh | |
| 2015/0143372 A1 | 5/2015 | Bercovici | |
| 2015/0150692 A1 | 6/2015 | Lye | |
| 2015/0182351 A1 | 7/2015 | Behzadi | |
| 2015/0272478 A1 | 10/2015 | Borja | |
| 2016/0038307 A1 | 2/2016 | Bettenga | |
| 2016/0100958 A1 | 4/2016 | Behzadi | |
| 2016/0135900 A1 | 5/2016 | Falardeau | |
| 2016/0157751 A1 | 6/2016 | Mahfouz | |
| 2016/0199199 A1 | 7/2016 | Pedicini | |
| 2016/0220315 A1 | 8/2016 | Falardeau | |
| 2016/0220318 A1 | 8/2016 | Falardeau | |
| 2016/0220385 A1 | 8/2016 | Falardeau | |
| 2016/0242934 A1 | 8/2016 | van der Walt | |
| 2016/0249968 A1 | 9/2016 | Walter | |
| 2017/0065429 A1 | 3/2017 | Behzadi | |
| 2017/0065430 A1 | 3/2017 | Singh | |
| 2017/0065431 A1 | 3/2017 | Singh | |
| 2017/0065432 A1 | 3/2017 | Singh | |
| 2017/0119475 A1 | 5/2017 | McCabe | |
| 2017/0172697 A1 | 6/2017 | Aghazadeh | |
| 2017/0172762 A1 | 6/2017 | Sherman | |
| 2017/0196506 A1 | 7/2017 | Behzadi | |
| 2017/0196701 A1 | 7/2017 | Behzadi | |
| 2017/0196704 A1 | 7/2017 | Behzadi | |
| 2017/0196705 A1 | 7/2017 | Behzadi | |
| 2017/0196706 A1 | 7/2017 | Behzadi | |
| 2017/0196707 A1 | 7/2017 | Behzadi | |
| 2017/0196708 A1 * | 7/2017 | Behzadi | A61B 17/1666 |
| 2017/0196710 A1 | 7/2017 | Behzadi | |
| 2017/0196711 A1 | 7/2017 | Behzadi | |
| 2017/0202682 A1 | 7/2017 | McCarthy | |
| 2017/0202683 A1 | 7/2017 | Behzadi | |
| 2017/0296274 A1 | 10/2017 | van der Walt | |
| 2017/0340456 A1 | 11/2017 | Behzadi | |
| 2017/0348059 A1 | 12/2017 | Kang | |
| 2017/0354368 A1 | 12/2017 | Behzadi | |
| 2017/0360575 A1 | 12/2017 | Behzadi | |
| 2018/0049622 A1 | 2/2018 | Ryan | |
| 2018/0055518 A1 | 3/2018 | Pedicini | |
| 2018/0055553 A1 | 3/2018 | Pedicini | |
| 2018/0055554 A1 | 3/2018 | Pedicini | |
| 2018/0078201 A1 | 3/2018 | Behzadi | |
| 2018/0078388 A1 | 3/2018 | Bettenga | |
| 2018/0092757 A1 | 4/2018 | Behzadi | |
| 2018/0125474 A1 | 5/2018 | Dougherty | |
| 2018/0168740 A1 | 6/2018 | Ryan | |
| 2018/0185107 A1 | 7/2018 | Nikou | |
| 2018/0193171 A1 | 7/2018 | van der Walt | |
| 2018/0250144 A1 | 9/2018 | Li | |
| 2018/0263704 A1 | 9/2018 | Lang | |
| 2018/0271601 A1 | 9/2018 | Meridew | |
| 2018/0296365 A1 | 10/2018 | Nielsen | |
| 2018/0303379 A1 | 10/2018 | Borja | |
| 2018/0303564 A1 | 10/2018 | Nikou | |
| 2018/0318017 A1 | 11/2018 | Fanson | |
| 2018/0333275 A1 | 11/2018 | Behzadi | |
| 2018/0338751 A1 | 11/2018 | Pedicini | |
| 2018/0338799 A1 | 11/2018 | Hladio | |
| 2018/0344414 A1 | 12/2018 | Nikou | |
| 2019/0125293 A1 | 5/2019 | Behzadi | |
| 2019/0133547 A1 | 5/2019 | Behzadi | |
| 2019/0133700 A1 | 5/2019 | Nikou | |
| 2019/0133701 A1 | 5/2019 | Nikou | |
| 2019/0175291 A1 | 6/2019 | Hagag | |
| 2019/0182555 A1 | 6/2019 | Olson | |
| 2019/0183554 A1 | 6/2019 | Pedicini | |
| 2019/0183555 A1 | 6/2019 | Pedicini | |
| 2019/0216521 A1 * | 7/2019 | Chhatrala | A61B 17/921 |
| 2019/0223889 A1 | 7/2019 | Pedicini | |
| 2019/0231446 A1 | 8/2019 | Bowling | |
| 2019/0282286 A1 | 9/2019 | Pedicini | |
| 2019/0290449 A1 | 9/2019 | Wu | |
| 2019/0343548 A1 | 11/2019 | Behzadi | |
| 2019/0350724 A1 | 11/2019 | Behzadi | |
| 2019/0350725 A1 | 11/2019 | Behzadi | |
| 2019/0350726 A1 | 11/2019 | Behzadi | |
| 2019/0350727 A1 | 11/2019 | Behzadi | |
| 2019/0350728 A1 | 11/2019 | van der Walt | |
| 2019/0357809 A1 | 11/2019 | Borja | |
| 2019/0357958 A1 | 11/2019 | Walter | |
| 2020/0008774 A1 | 1/2020 | Behzadi | |
| 2020/0015983 A1 | 1/2020 | Behzadi | |
| 2020/0015984 A1 | 1/2020 | Behzadi | |
| 2020/0022744 A1 | 1/2020 | Behzadi | |
| 2020/0030117 A1 | 1/2020 | Nic | |
| 2020/0046519 A1 | 2/2020 | Lim | |
| 2020/0069279 A1 | 3/2020 | Behzadi | |
| 2020/0069280 A1 | 3/2020 | Behzadi | |
| 2020/0069438 A1 | 3/2020 | Singh | |
| 2020/0155246 A1 | 5/2020 | Nikou | |
| 2020/0155247 A1 | 5/2020 | Nikou | |
| 2020/0197028 A1 | 6/2020 | Pedicini | |
| 2020/0268454 A1 | 8/2020 | Walter | |
| 2020/0294423 A1 | 9/2020 | Blain | |
| 2020/0352654 A1 | 11/2020 | van der Walt | |
| 2021/0093401 A1 | 4/2021 | Falardeau | |
| 2021/0220152 A1 | 7/2021 | Nielsen | |
| 2021/0228252 A1 | 7/2021 | Pedicini | |
| 2021/0244397 A1 | 8/2021 | Pedicini | |
| 2021/0259854 A1 | 8/2021 | Falardeau | |

(56) References Cited

U.S. PATENT DOCUMENTS

| | | | | |
|---|---|---|---|---|
| 2021/0315716 | A1 | 10/2021 | van der Walt | |
| 2021/0361336 | A1 | 11/2021 | Adekanmbi | |
| 2022/0071509 | A1 | 3/2022 | Borja | |
| 2022/0142693 | A1 | 5/2022 | Slocum | |
| 2022/0183735 | A1 | 6/2022 | Wallace | |
| 2022/0226033 | A1* | 7/2022 | Slocum | A61F 2/4603 |
| 2022/0234868 | A1 | 7/2022 | Feng | |
| 2022/0240947 | A1 | 8/2022 | Marinkovich | |
| 2022/0273317 | A1 | 9/2022 | Levy | |
| 2022/0313337 | A1 | 10/2022 | Pedicini | |
| 2023/0285062 | A1 | 9/2023 | Santos | |
| 2024/0024012 | A1* | 1/2024 | Dittrich | A61B 17/92 |

FOREIGN PATENT DOCUMENTS

| | | | |
|---|---|---|---|
| CN | 101272739 | A | 9/2008 |
| CN | 101351161 | A | 1/2009 |
| CN | 201422925 | Y | 3/2010 |
| CN | 101889897 | A | 11/2010 |
| CN | 204863450 | U | 12/2015 |
| DE | 102008043136 | A1 | 4/2010 |
| DE | 102010017726 | A1 | 1/2011 |
| DE | 102011077241 | A1 | 12/2012 |
| EP | 0290375 | A1 | 11/1988 |
| EP | 2658462 | A2 | 11/2013 |
| EP | 2846722 | A1 | 3/2015 |
| EP | 3162314 | A1 | 5/2017 |
| EP | 2658462 | B1 | 7/2017 |
| EP | 2846722 | B1 | 11/2017 |
| EP | 3242618 | A1 | 11/2017 |
| EP | 3284429 | A1 | 2/2018 |
| EP | 3300677 | A1 | 4/2018 |
| EP | 3356087 | A1 | 8/2018 |
| EP | 3162314 | B1 | 2/2019 |
| EP | 3517064 | A2 | 7/2019 |
| EP | 3300677 | B1 | 9/2019 |
| EP | 3566667 | A2 | 11/2019 |
| EP | 3569164 | A1 | 11/2019 |
| EP | 3629961 | A1 | 4/2020 |
| EP | 3723644 | A1 | 10/2020 |
| FR | 2054809 | A5 | 5/1971 |
| WO | 8802246 | A2 | 4/1988 |
| WO | 03068078 | A1 | 8/2003 |
| WO | 2008017648 | A1 | 2/2008 |
| WO | 2013169334 | A1 | 11/2013 |
| WO | 2016112397 | A1 | 7/2016 |
| WO | 2017123506 | A1 | 7/2017 |
| WO | 2018031752 | A1 | 2/2018 |
| WO | 2018128765 | A1 | 7/2018 |

OTHER PUBLICATIONS

Search Report for Application No. GB2016060.2, mailed Mar. 22, 2021, 5 pages.

International Search Report and Written Opinion dated Mar. 17, 2022, for the International Patent Application No. PCT/GB2021/052604 filed on Oct. 7, 2021, 19 pages.

European Patent Office, Partial European Search Report, Jun. 19, 2026, 15 pages.

* cited by examiner

IMPACTOR

CROSS-REFERENCE TO RELATED APPLICATIONS

This application is a continuation of pending U.S. patent application Ser. No. 18/193,116, filed on Mar. 30, 2023, which application is a continuation of International Application No. PCT/GB2021/052604, filed Oct. 7, 2021, which claims priority to UK Patent Application No. 2016060.2, filed Oct. 9, 2020, and also claims priority to UK Patent Application No. 2110224.9, filed Jul. 15, 2021, the entirety of which applications are incorporated by reference herein.

FIELD OF THE INVENTION

The present invention relates to an impactor, in particular an orthopaedic impactor, as well as methods of using and calibrating the impactor.

BACKGROUND TO THE DISCLOSURE

There are many situations in which it is desirable to affix two objects. One way to do this is using an impactor, which effects a force on a first object to drive it into (or pull it out of) the second object. Such an impactor may be used, for example, in orthopaedic procedures, such as total hip arthroplasties (THAs), which require an implant to be affixed to a bone. Conventional THA procedures affix an implant to the pelvic bone using a press fit. Specifically, a cavity is created in the pelvic bone; the implant is placed within that cavity; and the implant is impacted so that the implant is forced into the bone. This process generates hoop strain and creates friction at the implant-bone interface, which secures the implant.

Conventionally, the impacting force is delivered using a handheld mallet that is swung by a surgeon. While this is a relatively straightforward process that requires only simple equipment, this method of delivering force can result in an inconsistent force being applied to the implant. As a result, each THA procedure performed using a mallet is likely to have a different implanting force so that each implant is secured with a different stability. This is undesirable not least because if the implant is not adequately impacted by the surgeon there may be inadequate hoop strain, and this may prevent bony ingrowth. This is a particular problem during revision cases, where bone quality may be low. Conversely, if too much impact force is use, the implant may generate excessive strain in the bone, leading to a fracture.

To address this problem, powered impactor devices have been developed. A powered impactor can deliver a more consistent impacting force and can also reduce the physical exertion required by a surgeon.

U.S. Pat. No. 10,342,591 B2 discloses an orthopaedic impacting tool that includes a motor, an energy storage chamber, a striker, and an anvil. The motor stores energy in the energy storage chamber and then releases it, causing the striker to apply a controlled force on an adapter to create a precise impact for use in a surgical setting. As described by this document, the energy storage chamber can comprise a vacuum or compressed gas.

U.S. Pat. No. 10,342,591 B2 requires a pressurized energy storage chamber to be provided and maintained; this could lead to a bulky impacting tool and could result in problems if the integrity of the pressurized chamber is compromised. In particular, damage to the chamber during an operation could cause substantial damage to the patient or compromise the success of the surgery (e.g., if the escaping pressurised gas imparts an undesired lateral force on the implant).

SUMMARY OF THE DISCLOSURE

According to an aspect of the present disclosure, there is described: an orthopaedic impactor, comprising: a strike assembly arranged to impart a force to an object; and a winding arranged to receive a current and thereby induce a magnetic field; wherein the winding is arranged to interact with the strike assembly so that, in use, a magnetic field generated by the winding causes the strike assembly to move so as to impart the force to the object.

The use of a winding enables the rapid provision of a force to the object and also enables the frequency of impacts to be varied independently from the force of each impact.

According to an aspect of the present disclosure, there is described: an orthopaedic impactor, comprising: a strike assembly; a connector arranged to impart a force to an object; and a winding arranged to receive a current and thereby generate a magnetic field; wherein the winding, the strike assembly, and the connector are arranged so that, in use, a magnetic field generated by the winding causes the strike assembly to move so as to impact the connector; and wherein the connector is arranged to move between a first position and a second position such that: in the first position, when the strike assembly impacts the connector the connector imparts a force to the object in a first direction; and in the second position, when the strike assembly impacts the connector the connector imparts a force to the object in a second direction; wherein the first direction and the second direction are different.

Preferably, a body of the strike assembly comprises a ferromagnetic material arranged to be moved by the magnetic field.

Preferably, the winding is arranged to interact with the strike assembly such that the provision of a current causes the strike assembly to move.

Preferably, the winding is arranged to interact with the strike assembly such that the removal of a current causes the strike assembly to move.

Preferably, impactor comprises a connector is arranged to receive a force from the strike assembly and to impart a force to the object.

Preferably, the connector comprises a securing mechanism for securing the object.

Preferably, the securing mechanism comprises a grip for gripping the object.

Preferably, the strike assembly is arranged to move so as to impact the connector, preferably wherein the connector is arranged to be spaced from the strike assembly in a resting position.

Preferably, the connector is arranged to receive a first force from a first, proximal, striker of the strike assembly and the connector is arranged to receive a second force from a second, distal, striker of the strike assembly; wherein the direction of the first force differs from the direction of the second force.

Preferably, the connector is arranged to at least partially surround a/the striker of the strike assembly so as to receive the first force when the strike assembly moves in a first direction and the second force when the strike assembly moves in a second direction. Preferably, the second direction is opposite the first direction.

Preferably, the first force is an implanting force.

Preferably, the second force is a removing force.

Preferably, the connector is arranged to be substantially stationary during the use of the impactor.

Preferably, the connector is arranged to be spaced from the strike assembly in a resting position. Preferably, the impactor is arranged to be spaced by at least 3 mm, at least 5 mm, at least 10 mm, and/or at least 20 mm.

Preferably, the strike assembly weighs at least 0.6 kg, at least 1.2 kg, at least 1.8 kg, at least 2.5 kg, and/or at least 4 kg.

Preferably, the connector weighs no more than 1 kg, no more than 0.5 kg, no more than 0.2 kg, and/or no more than 0.1 kg.

Preferably, the strike assembly has a mass that is at least twice that of the connector, at least three times that of the connector, at least five times that of the connector, and/or at least ten times that of the connector.

Preferably, the strike assembly is arranged to be capable of moving at least 1 m/s, at least 1.5 m/s, at least 2 m/s, at least 3 m/s, and/or at least 5 m/s.

Preferably, the strike assembly and/or the connector is arranged to move between a first position and a second position, wherein the strike assembly and/or the connector imparts a/the first force wherein the strike assembly and/or the connector is in the first position and a/the second force when the strike assembly and/or the connector is in the second position.

Preferably, the impactor comprises a holding mechanism arranged to hold the strike assembly in the first position and/or the second position.

Preferably, in the first position a forward surface of the strike assembly abuts a surface of the impactor and in the second position a backward surface of the connector abuts a surface of the impactor.

Preferably, the impactor further comprises a power source for supplying the current to the winding. Optionally, the power source comprises a battery. Optionally, the power source comprises a capacitor. Optionally, the power source comprises both a battery and a capacitor.

Preferably, the impactor further comprises an input for altering a parameter of the force.

Preferably, the input is arranged to alter at least one of: a direction of the force; a magnitude of the force; a speed of the application of the force; a frequency of application of force; a duration of the force; and an energy of an impact relating to the force.

Preferably, the input is arranged to alter the current supplied to the winding in order to alter the parameter of the force. Preferably, the input is arranged to alter at least one of: a direction of the current; a magnitude of the current; a duration of the current; a frequency of the current; a frequency of transmission of pulses of current.

Preferably, the impactor comprises two inputs, wherein each input is arranged to alter a different parameter of the force. Preferably, a first input is arranged to alter a magnitude of the force and a second input is arranged to alter a speed of the force.

Preferably, the input comprises at least one of: a rotatable input; a slidable input; a variable input; and a touch-sensitive screen.

Preferably, the impactor is arranged to determine use data. Preferably, the use data comprises one or more of: a bone quality; an implant stability; an impact force; the difference between an impact force and a desired force; an impact frequency; a user of the device; and a hoop stress.

Preferably, the impactor is arranged to transmit the use data to an external server.

Preferably, the impactor further comprises control electronics arranged to alter the supply of current to the winding. Preferably, the control electronics is arranged to interact with one or more of: an/the input and a/the power source.

Preferably, the control electronics is arranged to alter the supply of current and/or a provided force based on a previous force imparted on the object and/or based on a property of the object. Preferably, the control electronics is arranged to alter the current and/or force based on one or more of: a determined bone quality; an implant stability; an impact force; the difference between a previously measured force and a desired force.

Preferably, the control electronics is arranged to alter the supply of current and/or a provided force based on one or more of: a previous use of the impactor; a user of the impactor and/or a property of the object being impacted.

Preferably, the control electronics comprises a feedback loop and/or a closed feedback loop.

Preferably, the control electronics comprises a proportional-integral-derivative (PID) controller.

Preferably, the strike assembly is arranged to move between a first, resting, position and a second, active, position. Preferably, at the first position the strike assembly is spaced from a/the connector and at the second position the strike assembly is in contact with a/the connector.

Preferably, the strike assembly is arranged to further move to a third, active, position.

Preferably, movement to the second position relates to the imparting of a force in a first direction and movement to the third position relates to the imparting of a force in a second direction.

Preferably, the strike assembly is arranged to move to either the second position or the third position in dependence on an external force placed on the impactor.

Preferably, the impactor comprises a plurality of spools. Preferably, the plurality of spools are arranged to provide forces of different magnitudes of force and/or forces in different directions.

Preferably, the plurality of spools comprises axially separated spools. Preferably, the plurality of spools comprises axially separated spools with a coincident central axis.

Preferably, the impactor comprises at least one spool located to a first side of the strike assembly and at least one spool located to a second side of the strike assembly.

Preferably, the first spool is arranged to move the strike assembly in a first direction and the second spool is arranged to move the strike assembly in a second direction. Preferably, the second direction is opposite the first direction.

Preferably, the plurality of spools comprises radially separated spools. Preferably, the plurality of spools comprises radially separated spools with a coincident central axis.

Preferably, the impactor further comprises a bearing arranged to support the strike assembly and/or a/the connector.

Preferably, the impactor further comprises a bearing holder arranged to limit the travel of a/the connector.

Preferably, the impactor further comprises a spacer arranged to limit the travel of the strike assembly and/or a/the connector.

Preferably, the impactor further comprises an end cap arranged to limit the travel of the strike assembly.

Preferably, the impactor further comprises a biasing mechanism. Preferably, the biasing mechanism comprises a spring.

Preferably, the biasing mechanism is arranged to bias the strike assembly towards a/the first, resting, position.

Preferably, the biasing mechanism is arranged to compress as the strike assembly is moved from the first position to a/the second, active, position and/or wherein the biasing mechanism is arranged to extend as the strike assembly is moved from the first position to a/the third, active, position.

Preferably, the second position relates to the provision of an implanting force and/or the third position relates to the provision of a removal force.

Preferably, the strike assembly is arranged to move so as to provide one or more of: an implanting force when the strike assembly is in a distal position and a current is provided to the spool; a removal force when the strike assembly is in a proximal position and a current is removed from the spool; an implanting force when the strike assembly is in the distal position and a current is removed from to spool; and a removal force when the strike assembly is in the proximal position and a current is provided to the spool.

Preferably, the biasing mechanism is arranged to exert a force to move the strike assembly to provide the implanting and/or removing force when the current is removed.

Preferably, the winding is arranged to provide a force that acts against, and/or counteracts, the biasing mechanism.

Preferably, the winding is arranged to act against the biasing mechanism such that, when a current is removed from the winding, the biasing mechanism interacts with the strike assembly so as to impart a force to the object.

Preferably, the winding comprises a solenoid and/or the winding comprises one or more loops of wire.

Preferably, the winding is arranged to radially surround a ferromagnetic body of the strike assembly throughout the range of travel of the body.

Preferably, the winding is arranged to axially surround a/the ferromagnetic body of the strike assembly throughout the range of travel of the body.

Preferably, a/the ferromagnetic body of the strike assembly body is axially spaced from the winding throughout part of, or the entirety of, the range of travel of the body.

Preferably, a/the striker of the strike assembly comprises a ferromagnetic material.

Preferably, the winding is arranged about a supporting member.

Preferably, a/the body of the strike assembly is located within the supporting member.

Preferably, a/the body of the strike assembly is constrained to move along a single axis. Preferably, the body is constrained by a/the supporting member.

Preferably, the connector is constrained to move along a single axis. Preferably, a/the body of the strike assembly of the strike assembly is constrained by a/the linear bearing.

Preferably, the impactor further comprises a casing surrounding one or more of the components of the impactor.

Preferably, the casing comprises a securing mechanism arranged to hold a/the connector in place at one or more positions. Preferably, the positions include: an implanting position and/or a removing position.

Preferably, the impactor is arranged to provide one or more of: an implanting force; and a removing force.

Preferably, a central axis of the winding is coincident with a central axis of the a/the body of the strike assembly.

Preferably, a central axis of the winding is coincident with a central axis of a/the connector.

Preferably, the impactor further comprises a sensor. Preferably, the sensor is arranged to measure at least one of: an impact force; an object stability; an implant stability; and an impact energy.

Preferably, the impactor further comprises a user interface for displaying at least one of: a parameter of the force; and a feature of the operation of the impactor.

Preferably, a/the body of the strike assembly comprises a ferromagnetic material. Preferably, the body comprises iron. Preferably, the body comprises at least 70% iron.

Optionally, a/the body of the strike assembly comprises a permanent magnet.

Preferably, the winding comprises a copper wire and/or the winding comprises at least 70% copper.

Preferably, the winding is arranged to provide a current for less than 1 s, less than 0.5 s, and/or less than 0.1 s.

Preferably, the winding comprises at least 300 turns; at least 500 turns and/or at least 800 turns.

Preferably, the winding is arranged to receive a current of at least 5 A, at least 8 A, at least 10 A, and/or at least 15 A.

Preferably, the impactor is arranged to provide an impact energy of less than or equal to 5 J, less than or equal to 3 J, less than or equal to 1 J, and/or less than or equal to 0.5 J.

Preferably, the impactor is arranged to provide an impact energy of greater than or equal to 10J, greater than or equal to 15 J, greater than or equal to 20 J, and/or greater than or equal to 30 J.

Preferably, the impactor is arranged to provide an impact force of less than or equal to 5 kN, less than or equal to 3 kN, less than or equal to 1 kN, and/or less than or equal to 0.5 kN.

Preferably, the impactor is arranged to provide an impact energy of greater than or equal to 20 kN, greater than or equal to 25 kN, greater than or equal to 30 kN, and/or greater than or equal to 50 kN.

Preferably, the impactor is arranged to provide an impact impulse of less than or equal to 2 Ns, less than or equal to 1 Ns, and/or less than or equal to 0.5 Ns.

Preferably, the impactor is arranged to provide an impact impulse of greater than or equal to 3Ns, greater than or equal to 5 Ns, and/or greater than or equal to 7 Ns.

Preferably, the impactor is arranged to provide an impact frequency of less than or equal to 3 Hz, less than or equal to 1 Hz, and/or less than or equal to 0.5 Hz.

Preferably, the impactor is arranged to provide an impact frequency of greater than or equal to 7 Hz, greater than or equal to 10 Hz, and/or greater than or equal to 15 Hz.

Preferably, a/the striker of the strike assembly comprises a hardened coating.

Preferably, a/the striker of the strike assembly comprises a coating. Preferably, a/the striker comprises a soft and/or flexible coating. Preferably, the coating is arranged to deform as the strike assembly imparts the force to the object.

Preferably, the impactor comprises an orthopaedic impactor. Preferably, the impactor comprises an orthopaedic impactor for performing total hip arthroplasty (THA).

Preferably, the impactor comprises a plurality of windings.

Preferably, the impactor comprises: one or more proximal impact windings arranged to provide a force in a first direction; and one or more distal winding arranged to provide a force in a second direction.

Preferably, the proximal impact windings are arranged to provide a greater impact energy and/or impact force to the object than the distal impact windings.

Preferably, the proximal impact windings have a greater volume, length, and/or surface area than the distal impact windings.

Preferably, the impactor comprises a greater number of proximal impact windings than distal impact windings.

According to another aspect of the present invention, there is described an orthopaedic impactor, comprising: a strike assembly arranged to impart a force to an object; and a plurality of windings arranged to receive a current and thereby generate a magnetic field; wherein the windings are arranged to interact with the strike assembly so that, in use, a magnetic field generated by the winding causes the strike assembly to move so as to impart the force to the object; wherein the impactor comprises: a plurality of proximal impact windings arranged to provide a force in a first direction; and one or more distal winding arranged to provide a force in a second direction; wherein the impactor comprises a greater number of proximal impact windings than distal impact windings.

Preferably, the proximal impact windings and distal impact windings are provided in an alternating arrangement.

Preferably, the impactor comprises two proximal windings and one distal winding, wherein the distal winding is located between the proximal windings.

Preferably, the impactor is arranged to use the winding as a sensor.

Preferably, the impactor is arranged to measure an operational parameter in dependence on a current and/or voltage in the winding.

According to an aspect of the present disclosure, there is described: an orthopaedic impactor, comprising: a strike assembly arranged to impart a force to an object; and a winding arranged to receive a current and thereby induce a magnetic field; wherein the winding is arranged to interact with the strike assembly so that, in use, a magnetic field generated by the winding causes the strike assembly to move so as to impart the force to the object; wherein the impactor is arranged to measure an operational parameter in dependence on a current and/or voltage in the winding.

Preferably, the impactor is arranged to determine at least one of: a position of the strike assembly; and a force of an impact in dependence on the current and/or voltage in the winding.

According to another aspect of the present disclosure, there is described an impactor comprising: a strike assembly; and a connector, the connector being arranged to receive a force from the strike assembly and to impart a force to an object; wherein the connector is arranged to be spaced from the strike assembly in a resting position.

Preferably, the connector is arranged to be spaced from the strike assembly in a resting position. Preferably, the impactor is arranged to be spaced by at least 3 mm, at least 5 mm, at least 10 mm, and/or at least 20 mm.

Preferably, the strike assembly weighs at least 0.6 kg, at least 1.2 kg, at least 1.8 kg, at least 2.5 kg, and/or at least 4 kg.

Preferably, the connector weighs no more than 1 kg, no more than 0.5 kg, no more than 0.2 kg, and/or no more than 0.1 kg.

Preferably, the strike assembly has a mass that is at least twice that of the connector, at least three times that of the connector, at least five times that of the connector, and/or at least ten times that of the connector.

Preferably, the strike assembly comprises a striker.

Preferably, the connector is arranged to at least partially surround the striker of the strike assembly and is arranged to receive a force from the striker and to impart a force to the object.

Preferably, the connector is arranged to move between a first position and a second position such that: in the first position, the striker impacts a first surface of the connector and the connector imparts a first force to the object in a first direction; and in the second position, the striker impacts a second surface of the connector such that the connector imparts a second force to the object in a second direction.

Preferably, the first direction and the second direction are different.

According to another aspect of the present disclosure, there is described a method of operating an impactor and/or operating the aforesaid impactor.

According to another aspect of the present disclosure, there is described a method of operating an impactor, the impactor comprising: a strike assembly arranged to impart a force to an object; and a winding arranged to receive a current and thereby induce a magnetic field;

wherein the winding is arranged to interact with the strike assembly so that, in use, a magnetic field generated by the winding causes the strike assembly to move so as to impart the force to the object, the method comprising: providing a current to the winding so as to generate the magnetic field; and/or removing a current from the winding so as to cease the generation of a magnetic field.

Preferably, the method comprises providing a current to the winding that is greater than a maximum operating current and/or a desired operating current of the winding.

Preferably, the method comprises providing a current to the spool when the current in the spool is below a lower limit.

Preferably, the method comprises halting the provision of a current to the spool when the current in the spool exceeds an upper limit.

Preferably, the method comprises determining that a current in the winding is approaching and/or exceeding the maximum operating current; and halting the supply of the current to the winding.

Preferably, the method comprises repeatedly providing and halting a current provided to the winding in order to maintain a current in the winding this is similar to and/or beneath the maximum operating current of the winding.

Preferably, the method comprises applying an initial force to the impactor.

Preferably, the impactor is arranged so that the direction of the force imparted by the impactor is dependent on the initial force applied to the impactor.

According to another aspect of the present disclosure, there is described a method of calibrating an impactor, the impactor comprising: a strike assembly arranged to impart a force to an object; and a winding arranged to receive a current and thereby induce a magnetic field;

wherein a body of the strike assembly comprises a ferromagnetic material; and wherein the winding surrounds the body so that, in use, a magnetic field generated by the winding causes the strike assembly to move so as to contact the connector; the method comprising: determining a property of a force imparted to an object during a use of the impactor; determining a difference between the property and a desire property; determining calibration information for modifying a future current that will be provided to the winding based on the difference.

According to another aspect of the present disclosure, there is described a method of operating an impactor, the impactor comprising: a strike assembly arranged to impart a force to an object; and a winding arranged to receive a current and thereby induce a magnetic field; wherein the winding is arranged to interact with the strike assembly so that, in use, a magnetic field generated by the winding causes the strike assembly to move so as to impart the force to the object, the method comprising: providing a current to the winding so as to generate the magnetic field; and/or removing a current from the winding so as to remove the magnetic field and/or cease the generation of the magnetic field.

Preferably, the method further comprises applying an initial force to the impactor.

According to another aspect of the present disclosure, there is described an orthopaedic impactor, comprising: a strike assembly comprising a striker; a winding arranged to receive a current and thereby generate a magnetic field; and a connector, wherein the connector is arranged to at least partially surround the striker of the strike assembly and is arranged to receive a force from the striker and to impart a force to an object; wherein the winding is arranged to interact with the strike assembly so that, in use, a magnetic field generated by the winding causes the strike assembly to move so that the striker impacts the connector; wherein the connector is arranged to move between a first position and a second position such that: in the first position, the striker impacts a first surface of the connector and the connector imparts a first force to the object in a first direction; and in the second position, the striker impacts a second surface of the connector such that the connector imparts a second force to the object in a second direction; wherein the first direction and the second direction are different.

According to another aspect of the present disclosure, there is described a method of operating an impactor, the impactor comprising: a strike assembly comprising a striker; a winding arranged to receive a current and thereby induce a magnetic field; and a connector, wherein the connector is arranged to at least partially surround the striker of the strike assembly and is arranged to receive a force from the striker and to impart a force to an object; wherein the winding is arranged to interact with the strike assembly so that, in use, a magnetic field generated by the winding causes the strike assembly to move so that the striker impacts the connector, the method comprising: locating the connector in either a first position or a second position; and providing a current to the winding so as to generate the magnetic field; and/or removing a current from the winding so as to cease the generation of a magnetic field; wherein: in the first position, the striker impacts a first surface of the connector and the connector imparts a first force to the object in a first direction; and in the second position, the striker impacts a second surface of the connector such that the connector imparts a second force to the object in a second direction; wherein the first direction and the second direction are different.

According to another aspect of the present disclosure, there is described a method of calibrating an impactor, the impactor comprising: a strike assembly comprising a striker; a winding arranged to receive a current and thereby induce a magnetic field; and a connector, wherein the connector is arranged to at least partially surround the striker of the strike assembly and is arranged to receive a force from the striker and to impart a force to an object; wherein a body of the strike assembly comprises a ferromagnetic material; and wherein the winding surrounds the body so that, in use, a magnetic field generated by the winding causes the strike assembly to move so that the striker impacts the connector, wherein the connector is arranged to move between a first position and a second position, wherein: in the first position, the striker impacts a first surface of the connector and the connector imparts a first force to the object in a first direction; and in the second position, the striker impacts a second surface of the connector such that the connector imparts a second force to the object in a second direction; wherein the first direction and the second direction are different, the method comprising: determining a property of a force imparted to an object during a use of the impactor; determining a difference between the property and a desire property; and determining calibration information for modifying a future current that will be provided to the winding based on the difference.

Any feature described as being carried out by an apparatus, an application, and a device may be carried out by any of an apparatus, an application, or a device. Where multiple apparatuses are described, each apparatus may be located on a single device.

Any feature in one aspect of the disclosure may be applied to other aspects of the invention, in any appropriate combination. In particular, method aspects may be applied to apparatus aspects, and vice versa.

Furthermore, features implemented in hardware may be implemented in software, and vice versa. Any reference to software and hardware features herein should be construed accordingly.

Any apparatus feature as described herein may also be provided as a method feature, and vice versa. As used herein, means plus function features may be expressed alternatively in terms of their corresponding structure, such as a suitably programmed processor and associated memory.

It should also be appreciated that particular combinations of the various features described and defined in any aspects of the disclosure can be implemented and/or supplied and/or used independently.

The disclosure extends to methods and/or apparatus substantially as herein described with reference to the accompanying drawings.

'Impact' as used herein may relate to an impact that acts to implant an object (e.g., drive the object into another object) and/or an impact that acts to remove an object (e.g., pull the object out of another object).

The disclosure will now be described, by way of example, with reference to the accompanying drawings.

DESCRIPTION OF THE PREFERRED EMBODIMENTS

Figure 1:
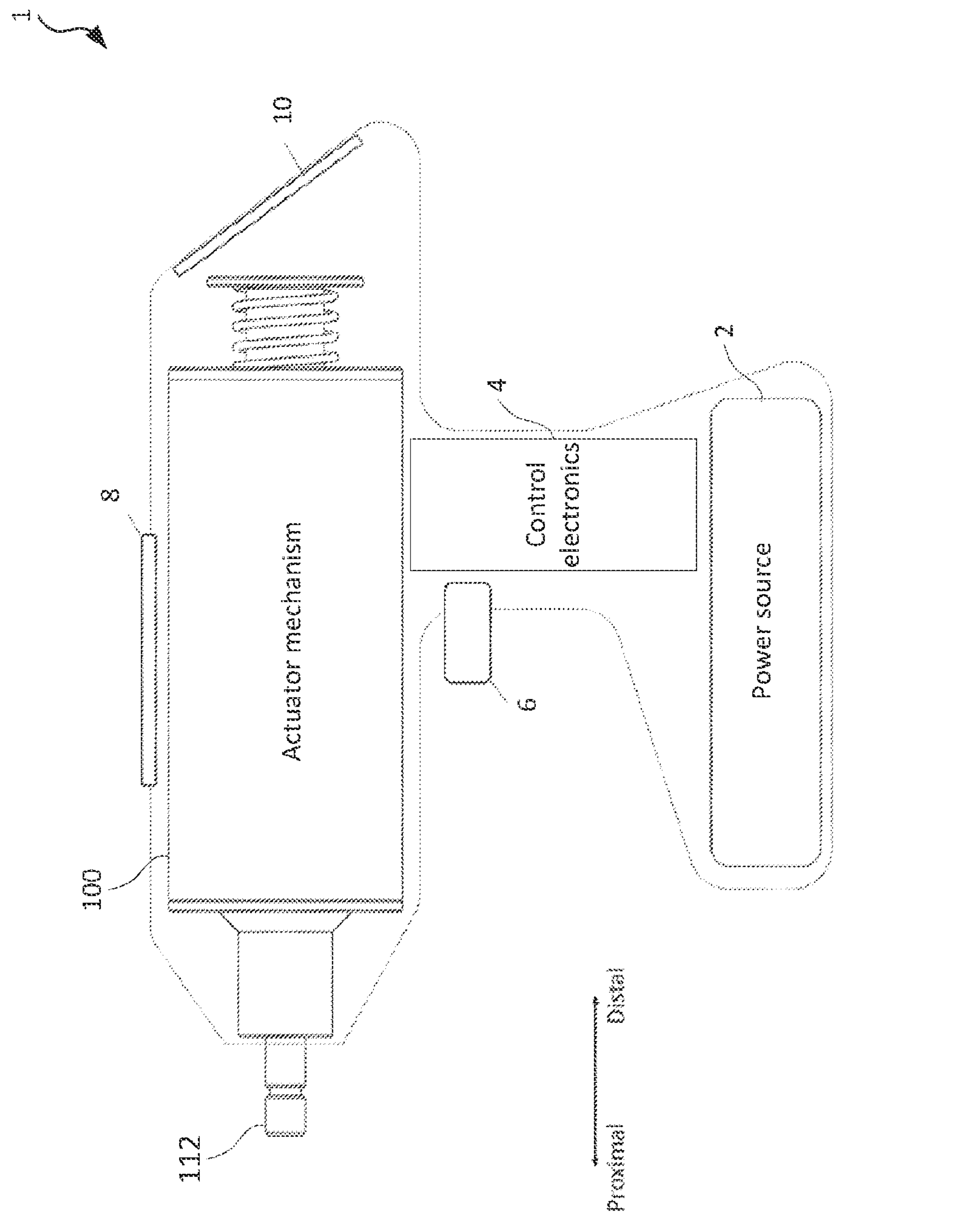
FIG. 1 shows an impactor.

Referring to FIG. 1, there is shown an impactor 1 that comprises a power source 2, control electronics 4, a primary input 6, a secondary input 8, a display, 12, and an actuator mechanism 100. The actuator mechanism comprises a connector 112.

The power source 2 is arranged to provide power to the other components. The power source typically comprises a lithium-ion battery. However, in various embodiments, the power source also, or alternatively, comprises: a capacitor, a supercapacitor, an interface for receiving mains power, an external power source, and/or a chemical power source. Combining a battery and a capacitor/supercapacitor enables the provision of a large power source that can, via charging a capacitor, provide a large instantaneous or short-term current. Typically, the power source comprises an internal battery, so that the impactor is portable. This internal battery may then be charged between uses (e.g., using a connection to mains power).

The control electronics 4 comprises a CPU that is arranged to execute instructions. The control electronics may also comprise: a memory (e.g., ROM or RAM) for storing information such as instructions for the CPU; a mass storage for storing larger amounts of information (e.g., an HDD); and/or a communications interface for communicating with other components or with external devices (e.g., a USB port or a wireless area network connector). More generally, the impactor 1 and/or the control electronics typically comprises a computer device (which may comprise one or more microcontrollers) that is arranged to control and co-ordinate the electric components of the impactor.

The primary input 6 and the secondary input 8 enable a user to vary the parameters of an impact provided by the impactor 1. The primary input typically comprises a force input that enables a user of the impactor to vary a force of impact. The secondary input typically comprises a speed input that enables a user of the impactor to vary a speed of impact. In some embodiments, only a single input is provided (which may control only a single impact parameter or may simultaneously control a plurality of parameters). In some inputs more than two inputs are provided. In some embodiments, a user interface (e.g., a touch-sensitive display) is provided which enables the precise control and observation of a range of impact parameters. Parameters that may be controlled by the inputs include: speed of impact; force of impact; frequency of impact; direction of impact (e.g., whether to drive in an implant or pull out an implant); depth of implant (e.g., how far into a bone an implant is to be driven); and stability of implant (e.g., as may be measured by hoop stress). These parameters may relate to a single impact or to a plurality of impacts; typically, achieving a desirable stability requires multiple impacts. Each input feeds information to the control electronics 4, which alters the operation of the actuator mechanism 100 accordingly to achieve the input parameters. The screen 10 provides a user interface through which a user of the impactor 1 is able to view information relating to the impactor. This information may relate to impact parameters (e.g., the input force/speed of impact), to the operation of the impactor (e.g., a remaining battery level), or to the impact performance of the impactor (e.g., a number of impacts that have occurred, a determined impact stability, or a total impact energy that has been transferred to an implant).

The actuator mechanism 100 receives instructions from the control electronics 4 and imparts a force to the connector 112 in accordance with the input impact parameters. The connector is arranged to impact an object so as to affix this object to, or remove this object from, a further object.

Typically, the actuator mechanism 100 comprises a winding, coil, or spool of wire. Typically, this winding forms a solenoid. The actuator mechanism 100 further comprises a ferromagnetic body located internally to the spool. The spool is arranged to induce a magnetic field when a current is passed through the wire. This magnetic field places a force on the body that results in the body interacting with the connector 112 so that the connector can place a force on an object.

The impactor 1 typically comprises an orthopaedic impactor that is used to affix or remove implants from bones. In particular, the impactor may be suitable for total hip arthroplasties (THAs). More generally, the impactor may be arranged to provide a driving force or a pulling/removal force to a broad range of objects. As an example, the impactor could be used to drive or remove nails. It will be appreciated that the components of the impactor may be configured for an intended purpose of the impactor. For example, where the impactor is used to drive nails, a connector may be used that is capable of securing a nail.

The remainder of the description refers to a 'distal' end and a 'proximal' end of the impactor 1; the distal and proximal directions are shown in FIG. 1. The proximal end of the impactor is that from which the connector 112 protrudes (the end proximate to the object being impacted) and the distal end is that nearer by a user. In use, the proximal end of the impactor is placed next to an object; the connector is placed in contact with the object; and the actuator mechanism 100 is operated in order to impart a force on the object (e.g., to drive an implant into a bone).

Typically, the connector 112 and/or the object comprises an attachment structure and/or mechanism that is arranged to secure the connector to the object. For example, the object may comprise a click-fit or snap-fit attachment structure into which the connector is pressed.

Where the connector comprises the attachment structure and/or mechanism, this attachment structure/mechanism may comprise one or more of: a gripping structure (e.g., a clamp); a snap-fit structure; an interference-fit structure; a magnetic attachment mechanism; a releasable attachment mechanism; and/or an interchangeable attachment structure/mechanism. In some embodiments, the connector is arranged to be used with a plurality of attachment structures, e.g., a snap-fit structure may be used when implanting an object and a gripping structure may be used for removing an object. The connector being arranged to be used with a plurality of attachment structures may also be beneficial since manufacturers of different implants may require different attachment structure.

Figure 2B:
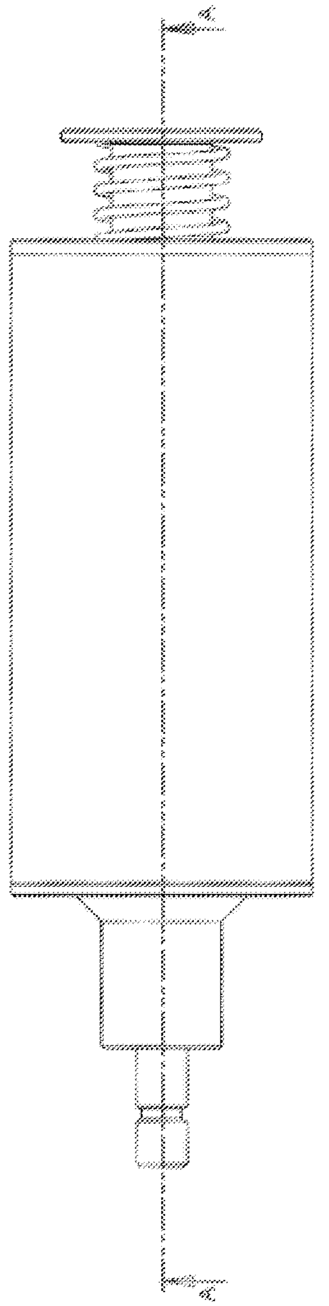
FIGS. 2*a*-2*c* show various views of an actuator mechanism of the impactor.
Figure 2A:
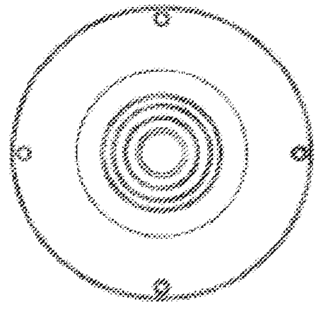
Figure 2C:
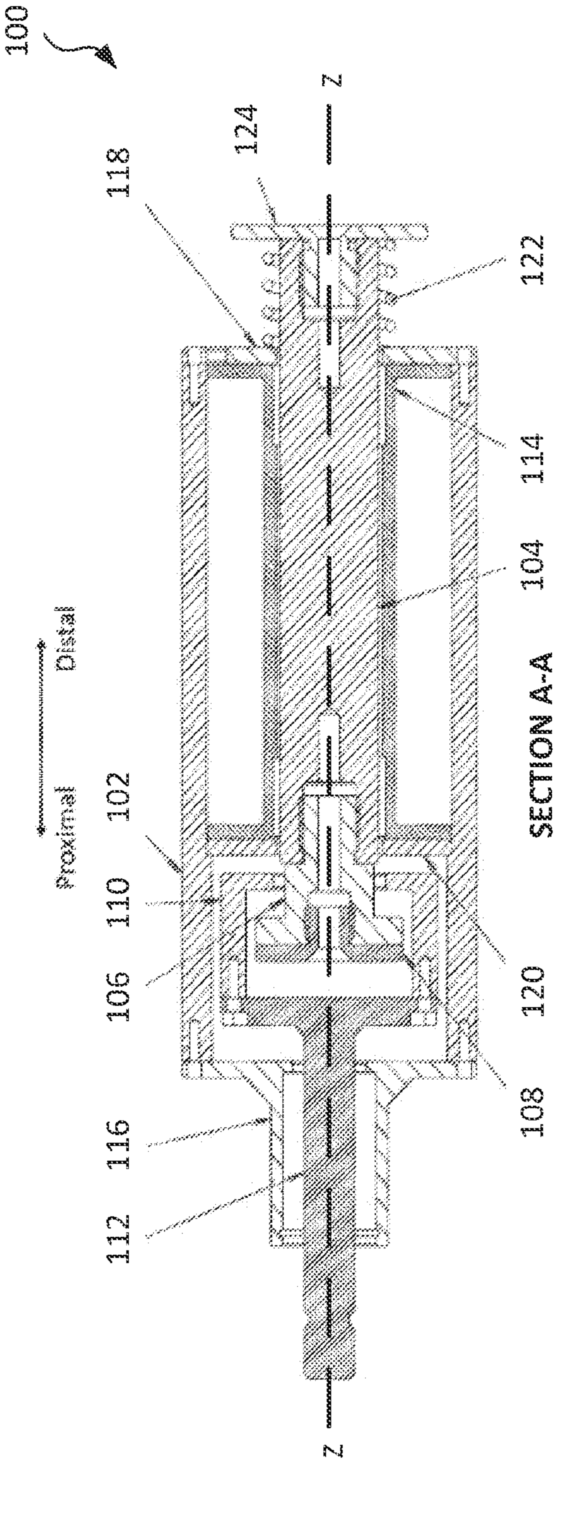

Referring to FIGS. 2*a*-2*c*, an embodiment of the actuator mechanism 100 is shown; specifically, an end-on view of the actuator mechanism is shown alongside a side-on view and a cross-sectional view.

The actuator mechanism 100 comprises a casing 102, a body 104, a distal striker 106, a proximal striker 108, a strike chamber 110, the connector 112, a spool 114, a bearing holder 116, an end cap 118, a spacer 120, and a return spring 122, and a cap 124.

The casing 102 is arranged to house, protect, and hold in place the other components of the actuator mechanism 100.

The body 104 is arranged to move the distal striker 106 when the body 104 is moved, which distal striker then moves the proximal striker 108, which proximal striker then impacts the connector 112. In this way, the body is able to transmit a force to the connector. Together, the body 104, the distal striker 106, and the proximal striker 108 comprise a strike assembly. In the following description, references to a movement of the body comprise references to a movement of the strike assembly and vice versa.

The body 104 is arranged to be moved by a magnetic field and typically comprises a ferromagnetic material. In order to efficiently transmit a force to the connector 112 via the distal striker 106 and the proximal striker 108 it is desirable for the body to comprise a material of substantial density (e.g., greater than 5 grams per cubic centimetre). For these reasons, the body typically comprises a high percentage of iron (e.g., greater than 70% iron by weigh, greater than 80% iron by weight, or greater than 90% iron by weight). Typically, the ferromagnetic material comprises a material with a high magnetic permeability (e.g., greater than $1\times10^{-5}$ H/m, greater than $1\times10^{-4}$ H/m, or greater than $1\times10^{-3}$ H/m). In some embodiments, the body comprises a permanent magnet. In some embodiments, the body comprises a ferromagnetic material that is arranged to be magnetised by the spool 114.

The distal striker 106 is arranged move with the body 104. Typically, this comprises the distal striker being connected to the body (e.g., via a rigid connector or by the distal striker being an integral part of the body). In this embodiment, the distal striker 106 is implanted in the body 104.

The proximal striker 108 is arranged to move as the distal striker 106 moves. This may comprise the proximal striker being an integral part of the distal striker and/or the body. This may comprise the proximal striker being rigidly connected to the distal striker.

Typically, the distal striker 106 and the proximal striker 108 are integral parts of a single striker component and so the distal and proximal striker may be thought of as two parts of a single striker.

Each of the body 104, the distal striker 106, and the proximal striker 108 may comprise the same materials and/or may comprise different materials. Since the distal striker and the proximal striker impact other components, the strikers may comprise a hard material and/or a hard coating to prevent damage to the strikers. Furthermore, the strikers may comprise a non-ferromagnetic (e.g., plastic material) to prevent any forces being placed on the strikers by the spool 114.

In some embodiments, one or more of the body 104, the distal striker 106 and the proximal striker 108 comprises a deformable, flexible and/or soft material (e.g., a plastic, a polymer, or a rubber coating). Such a material can reduce the peak force applied by the impactor so as to reduce the possibility of a fracture. The peak force may also be controlled by controlling the current provided to the spool 114, where a damping force may be applied to the body 104 using the spool to reduce the peak force of impact and/or lengthen the duration of an impact.

The strike chamber 110 comprises a chamber in which the proximal striker 108 impacts the connector 112. In a resting position (before an impact), there is typically a gap between the proximal striker and the connector. Once the body 104 moves, the proximal striker also moves (via the distal striker 106); specifically, the proximal striker moves towards the connector 112 through the strike chamber and then strikes the connector.

The strike chamber 110 may be arranged to be stationary within the casing 102 (e.g., the strike chamber may be fixed to the casing) or the strike chamber may be arranged to move with the connector 112 (e.g., the strike chamber may be connected to the connector). Indeed, typically, the strike chamber 110 is fixed to the connector (e.g., the strike chamber and the connector may be an integral part or may be secured together).

The connector 112 is arranged to be impacted by the proximal striker 108 and to then transfer this impact to an object. The connector typically comprises a dense, tough, and/or hard material (e.g., iron and/or steel) and/or a hardened coating to enable the connector to undergo repeated impacts without structural damage or excessive vibration.

In some embodiments, the connector 112 is arranged to secure an object (e.g., an implant). This enables a removal force to be applied to the object as well as an implanting force and can enable the object to be secured laterally so that the object is forced directly into or out of the bone (e.g. so that the impacting is entirely in the proximal-distal direction and/or is entirely in line with one or more of: a central axis of the connector, a central axis of the body 104, and a central axis of the spool 114). The securing mechanism may comprise a grip, a magnet, and/or an adhesive. The securing mechanism may comprise a quick-release mechanism arranged to rapidly grasp or release an object.

Each object with which the impactor 1 is used may require a different securing mechanism. Therefore, in some embodiments the connector 112 is removable and/or interchangeable. This enables the same impactor to be used with a variety of implants. Equally, the connector may be arranged to be used with a plurality of attachment structures or mechanisms (where these structures/mechanisms may be attached to the end of the connector) to enable use with different objects.

The spool 114 comprises a spool of wire that is placed around the body 104 and is arranged to receive a current from the power source 2. Typically, the spool 114 forms a solenoid. Typically, the spool comprises a material with a high electrical conductivity, such as copper.

In some embodiments, the spool 114 is arranged to surround the body 104 (or a ferromagnetic portion of the body) through the entire range of travel of the body. This may comprise the axial length of the spool being greater than 50%, greater than 75%, or greater than 100% of the axial length of the body. This ensures that a consistent force can be placed on the body throughout the travel of the body.

The body 104 may be axially offset (and spaced) from the spool in a resting position and/or may be axially offset from the centre of the spool (while still being radially surrounded and/or axially surrounded by the spool). Typically, the body is arranged to be axially closer to one end of the spool 114 than the other in a resting position; for example, the body may be nearer the distal end of the spool. Therefore, as the spool is energised, a magnetic force is placed upon the body that acts to draw the body into the spool (along the centreline of the spool). By ensuring that the axes of the body and the spool are aligned, it can be ensured that no undesirable radial force is placed on the body.

In some embodiments, a portion of the body 104 is arranged to extend beyond the spool 114 and/or to be axially offset from the centre of the spool. In particular, when a non-permanent magnet is used for the body, the body typically extends beyond the spool or is axially offset from the centre of the spool. A current being provided to the spool will generate a magnetic field. The current will also induce a current in the body leading to the generation of a further magnetic field that opposes the magnetic field generated by the spool. This can be used to impart a force on the body (and the strike assembly). In some embodiments, a/the ferromagnetic portion of the body or strike assembly is located outside of the spool (in the distal-proximate axis). As an example, the strikers 106, 108 may comprise a ferromagnetic material while the ‘body’ 104 of FIGS. 2*a*-2*c* does not. In this example, the strikers may be considered to comprise the body of the strike assembly by dint of their comprising the ferromagnetic material. The provision of a current in the spool 114 can then be used to force the strikers towards/away from the spool to provide a force to the connector 112.

As will be explained further below, the magnetic field generated by the spool can be used to provide an implanting force and/or a removing force by adjusting the arrangement of the strike assembly and the connector.

The flow of current through the spool 114 leads to a magnetic field being induced. Due to the placement of the spool 114 about the body 104, this magnetic field effects a force on the body 104. This force acts to move the body, and therefore the proximal striker 108, so that the proximal striker impacts the connector 112. The force placed on the magnetic field is dependent on the properties of the spool and the current flowing through the spool. In order to vary the magnetic force placed on the body—and therefore the impact parameters—the control electronics 4 is arranged to control the transfer of current from the power source 2 to the spool 114 (e.g., the magnitude of current flow, the duration of current flow, and/or the direction of the current flow) depending on the primary input 6 and the secondary input 8.

The properties of the spool 114 (e.g., the number of loops, the loop spacing, the wire thickness, and the wire material) may be selected based on a desired impact force. In some embodiments, the user is able to modify the properties of the spool, such as the number of loops of the spool or the spool spacing, in order to alter a force placed on the body 104.

In particular, the arrangement of, and the inputs to, the spool 114 enables variation of:

- The force of impact. By varying the period that current is applied to the spool, the time for which a magnetic force is applied to the body 104 can be varied. This enables a force to be applied for a long time (to cause a high force impact) or force to be applied for a short time (to cause a lower force impact). Similarly, the magnitude of the current applied can be varied. Applying a large current will result in a large force acting on the body and therefore a high force impact; applying a smaller current will result in a smaller force acting on the body and a lower force impact. Equally, a frequency of the current may be altered, where a higher frequency current will result in a greater impact force.
- The frequency of impact. Typically, current is applied to the spool 114 in pulses so that the connector 112 repeatedly impacts an implant. The frequency of impacts can be altered by altering the frequency of the pulses. Equally, a continuous current can be applied to the spool 114 to cause a continuous driving, or removing, force to be applied to an implant.
- The direction of impact. By altering the direction of the current entering the spool 114, the direction of the force placed on the body 104 can be altered. This enables a driving force or a removing force to be applied depending on the direction of the current.

Typically, the spool 114 has one or more of the following properties:

- Being comprised of copper, e.g., copper wire. The spool may comprise 75% copper, 90% copper and/or substantially 100% copper.
- Comprising at least 300 turns, at least than 500 turns, and/or at least than 800 turns (a turn being a single coil that surrounds the body 104).
- A current rating of at least 5 amps, at least 8 amps, at least 10 amps and/or at least 15 amps. Typically, the power source 2 is capable of providing at least 5 amps, at least 8 amps, at least 10 amps and/or at least 15 amps to the spool.
- A length of at least 50 mm, at least 80 mm, and/or at least 100 mm.
- A diameter of at least 40 mm, at least 55 mm, and/or at least 70 mm.

Typically, the spool 114 is arranged to:

- Provide an impact and/or removal force of less than or equal to 5 kN, less than or equal to 3 kN, less than or equal to 1 kN, and/or less than or equal to 0.5 kN.
- Provide an impact and/or removal force of greater than or equal to 20 kN, greater than or equal to 25 kN, greater than or equal to 30 kN, and/or greater than or equal to 50 kN.
- Provide impact and/or removal forces in the range of 0.5 kN-50 kN and/or 1 kN-30 kN.
- Provide an impact and/or removal energy of less than or equal to 5 J, less than or equal to 3 J, less than or equal to 1 J, and/or less than or equal to 0.5 J
- Provide an impact and/or removal energy of greater than or equal to 10 J, greater than or equal to 15 J, greater than or equal to 20 J, and/or greater than or equal to 30 J.
- Provide impact and/or removal energies in the range of 0.5 J-30 J and/or 1 J-20 J.
- Provide an impact and/or removal impulse of less than or equal to 2 Ns, less than or equal to 1 Ns, and/or less than or equal to 0.5 Ns.
- Provide an impact and/or removal impulse of greater than or equal to 3 Ns, greater than or equal to 5 Ns, and/or greater than or equal to 7 Ns.
- Provide impact and/or removal impulses in the range of 0.5 Ns-7 Ns and/or 1 Ns-5 Ns.
- Provide an impact and/or removal frequency (a number of impacts per second) of less than or equal to 3 Hz, less than or equal to 1 Hz and/or less than or equal to 0.5 Hz.
- Provide an impact and/or removal frequency of greater than or equal to 7 Hz, greater than or equal to 10 Hz and/or greater than or equal to 15 Hz.
- Provide impact and/or removal frequencies in the range of 0.5 Hz-15 Hz and/or 1 Hz-10 Hz.

Typically, the spool 114 is arranged to provide 'semi-automatic' impacts, e.g., a user is able to activate the spool to provide a single impact and then activate the spool again to provide another impact. Equally the spool may provide 'automatic' impacts, e.g., a user is able to hold down a trigger to provide repeated impacts. The frequency and number of impacts may also be controlled by the control electronics 4, where a user is able to input one or more of: an impact frequency; a number of impact; a desired stability; and a desired total impact energy and the control electronics provides an appropriate current to the spool. This enables a user to input use parameters before beginning an impact or removal and thereafter the energising of the spool proceeds automatically.

Using the spool 114, the impact force and the impact frequency can be varied independently. In particular, there is no need to recharge an impacting mechanism—if desired, multiple impacts (e.g., of different force) could be provided with essentially no pause between impacts.

Typically, an axis of the spool 114 (e.g., the central axis of the solenoid) is aligned with an axis of the body 104 (e.g., the central axis of the body). Typically, these axes are coincident. Typically, the same axis of the spool (e.g., the central axis of the solenoid) is aligned with an axis of the connector 112 (e.g., the central axis of the body). Typically, these axes are coincident.

Typically, the body is a cylindrical component that is located within the spool; the axes of each of these components being coincident then leads to the spool being capable of exerting a force on the body that is aligned with the axis of: the spool, the body, and the connector 112. This prevents an undesirable lateral force being placed on the implant.

The coincident axis of the body 104, the spool 114, and the connector 112 is shown in FIG. 1 as axis Z-Z. The distal striker 106 and the proximal striker 108 may also have a central axis that is coincident with this axis Z-Z.

Typically, the actuator mechanism 100 is rotationally symmetric and/or circularly symmetric about a central axis (e.g., the axis Z-Z). This ensures that the force provided does not depend on the angle at which the impactor 1 is being held.

The spool 114 is typically wrapped around a supporting component, where the body 104 is located internally to this supporting component and the body is able to move within this supporting component. The supporting component may be smooth and/or lubricated in order to aid movement of the body within the supporting component. The body typically fits snugly within the supporting component; this enables the supporting component to be used to ensure that the body remains aligned with the connector 112 so that no lateral force (perpendicular to the proximal-distal axis) is imparted to the connector. Similarly, the supporting component may be used to ensure that the central axis of the spool 114 remains aligned with an axis of the body and/or an axis of the connector.

The bearing holder 116 supports a linear bearing that guides the connector 112. The linear bearing ensures that the connector does not substantially move perpendicular to the forwards-backwards direction and also helps to support the connector as the connector moves (either in the proximal direction to drive an implant into a bone or in the distal direction to remove an implant from a bone). The linear bearing lets the strike assembly move freely as an implant is driven or removed while also ensuring that the force provided by the connector is entirely along the proximal-distal axis. In some embodiments, the distal end of the bearing holder is used to limit the movement of the connector. This may equally be thought of as the casing 102 abutting, and limiting the movement of, the connector since the bearing holder is typically a part of the casing. Specifically, as the connector moves in the proximal direction a surface of the connector is arranged to impact the bearing holder to define a maximum proximal displacement of the connector (and the striker assembly)—i.e., a maximum extension of the connector out of the impactor 1.

The end cap 118 constrains the spool 114 near the distal end of the impactor 1.

The spacer 120 constrains the spool 114 near the proximal end of the impactor 1. Together, the end cap 118 and the spacer form a boundary for the spool. The spacer also prevents excessive movement of the distal striker 106 when the body moves from in the distal direction. Specifically, as the body (and the distal striker) moves in the distal direction a rear surface of the distal striker is arranged to impact the spacer to define a maximum distal displacement of the striker assembly (and the connector 112).

The return spring 122 is arranged to provide a force to return the body 104 (and the striker assembly) from a proximal position to a resting position. The return spring is arranged to be compressed as the striker assembly is moved from the resting position to the proximal position (in order to contact the connector). In use, a current is provided to the spool 114 in order to place a force upon the body 104 so that the proximal striker 108 contacts the connector 112. When (or before) the proximal striker has impacted the connecter, the flow of current to the spool is halted and the compressive force in the return spring acts to return the body to a distal position. In some embodiments, the return spring 122 is not used and a return force is provided by reversing the direction of the current in the spool and/or providing an elastic surface.

Similarly, the return spring 122 may be arranged to extend when the body 104 is moved from a resting position to a distal position (e.g., to remove an implant).

The cap 124 is attached to the distal end of the body 104 and is used to hold the return spring 122 in place. Specifically, the return spring is held between the casing 102 and the cap so that as the body moves from the backwards position (or resting position) to the forwards position the return spring is compressed. This enables the return spring to provide a return force that returns the body to the resting position once a magnetic force placed on the body by the spool 114 is removed.

Typically, the body 104 (and the striker assembly) is arranged to move between a resting position and an active position. These positions may differ depending on a mode of the impactor 1 (e.g., whether the impactor is in a driving/impacting or removing mode).

In an impacting mode, at the resting position the proximate striker 108 is distanced from the connector 112 and at the active position the proximate striker contacts the connector. Therefore, as the striker assembly moves from the resting position to the active position, the connector is impacted by the proximate striker and drives the implant into the bone. The proximate striker can then be returned to the resting position (e.g., by a compressive force exerted by the return spring 122) to ready the impactor 1 for another impact.

In a removing mode, at the resting position the distal striker 106 is distanced from the strike chamber 110 and at the active position the distal striker contacts the strike chamber. Therefore, as the striker assembly moves from the resting position to the active position, the strike chamber is impacted by the proximate striker and the connector (which is connected to the strike chamber) removes the implant from the bone. The distal striker can then be returned to the resting position (e.g., by a tensile force exerted by the return spring 122) to ready the impactor 1 for another impact.

The resting position may depend on the mode, so that in the driving mode the body 104 may be located towards the distal end of the impactor 1 in the resting position and in the removing mode the body may be located towards the proximal end of the impactor in the resting position.

In some embodiments, the impactor 1 has a resting position that is in between a 'forward' active position (where the proximal striker 108 contacts the connector 112) and a 'backwards' active position (where the distal striker 106 contacts the strike chamber 110). From the resting position the body 104 can be moved towards the forward position to provide an implanting force; equally, the body can be moved towards the backwards position to provide a removal force.

In such embodiments, the return spring 122 may be arranged to compress as the body is moved from the resting position to the forwards position and to extend as the body is moved from the resting position to the backwards position. Therefore, in either position, the return spring acts to return the body 104 to the resting position.

In order to avoid the body 104 overshooting the resting position, a damping component may be included in the impactor 1 that damps the movement of the body. This damping component may be a part of the linear bearing supported by the bearing holder 116. In some embodiments, the spool 114 is used to provide the damping force to avoid the body overshooting the resting position (e.g., by providing a current to the spool in order to induce a damping magnetic field). The damping force is typically arranged to be applied so that the body is critically damped or over-damped.

In some embodiments, the damping force is only applied once the body is being returned from an active position (either the forwards position or the backwards position) to the resting position. This can be achieved using the spool 114. A current is supplied to the spool to move the body 104 from the resting position to either the forwards or backwards position; once the body has reached this position (and the connector has provided an implanting or removing force) the current is removed and the return spring 122 acts to return the body to the resting position. At this point, a current may be supplied to the spool to provide a damping force.

In order to return the connector 112 to a resting position following an impact from the proximal striker 108, the distal striker 106 may be arranged to impact the striker chamber 110 as the body 104 moves from the forwards position to the resting position. This may involve the body overshooting the resting position. The strike chamber being connected to the connector results in the connector being moved backwards with the strike chamber (towards the distal end of the impactor 1) after it is impacted by the distal striker 106.

In some embodiments, the bearing holder 116 is used to restrict the forward movement of the impact assembly; specifically, the contact of the connector 112 on the bearing holder and the proximal striker 108 on the connector can form the limit of movement for the proximal striker. In some embodiments, the return spring 122 can be used to restrict the forward movement of the impact assembly; specifically, the return spring can be selected so that the compression of the spring limits the movement of the body (where the return spring acts on the body via the cap 124).

In some embodiments, the connector 112 moves during use (e.g., the connector moves from the resting position to the active position after it is impacted). In some embodiments, the connector is arranged to be substantially stationary during use. For example, to impart an impacting force, the connector may be held in an active position and then struck by the proximal striker 108 (as the proximal striker moves from a resting position to an active position). The force imparted to the connector is by the proximal striker then transferred to an implant contacted by the connector.

Locating the connector 112 at the active position for implanting an object typically involves a force being placed on the connector to place the body in a rearmost position (e.g., a most distal position) where the distal striker 106 is in contact with the rear of the strike chamber 110 and the strike chamber is in contact with the spacer 120. Such a force occurs when the connector is pressed against an implant so as to force the implant into a bone.

Similarly, where the impactor 1 is being used to remove an implant, a force is typically imparted on the body 104 to move the body in a foremost position (e.g., a most proximal position). In this position, the connector 112 is in contact with the rear of the bearing holder 116 and the proximal striker 108 is in contact with the connector. The distal striker 106 is then spaced from the rear of the strike chamber 110. A force applied to the distal striker then causes the distal striker to move and striker the strike chamber so as to impact a removing force to the connector.

Figure 3A:
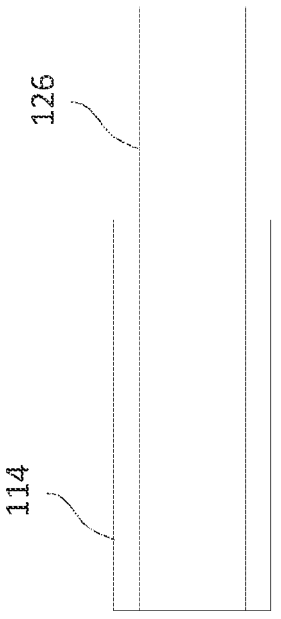
FIGS. 3*a*-3*d* show various embodiments of the actuator mechanism.

The above description referring to FIGS. 2*a*-2*c* has described a detailed embodiment of the actuator mechanism 100. Referring to FIG. 3*a*, in a simpler embodiment the actuator mechanism 100 comprises:

- A strike assembly 126, which strike assembly typically comprises a ferromagnetic material. Typically, the strike assembly comprises the body 104 and one or more strikers. The strikers may be arranged to impact a connector and/or may be arranged to directly impact an object. The strikers may be arranged to provide both an implanting force and a removing force.
- A spool 114 (and/or a winding, coil and/or solenoid). The spool is arranged to place a (magnetic) force on the strike assembly 126 when a current is provided to the spool. This strike assembly is arranged to move as a result of this magnetic force (e.g., to impact an object).

Figure 3B:
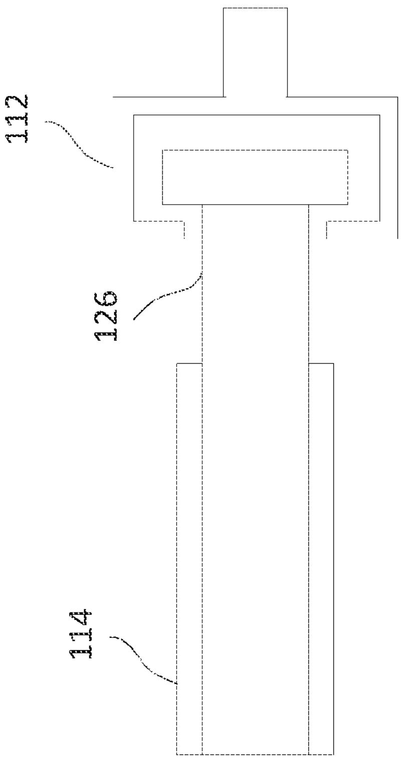

Referring to FIG. 3*b*, the actuator mechanism 100 typically further comprises the connector 112. The connector is arranged to be impacted by a striker of the strike assembly 126 and to transfer the impact force to an object. The connector may be arranged to provide a force in only a single direction (and may be located entirely to one side of the strike assembly). Alternatively, the connector may be arranged to provide a force in either direction. In this case, the connector is arranged to at least partially surround a component of the strike assembly as shown in FIG. 3*b*, this enables different forces to be provided by moving the strike assembly in different directions. More specifically, the connector typically comprises and/or is attached to, the strike chamber 110, wherein the striker(s) of the strike assembly are located within the strike chamber. This enables the strikers to move: proximally to impact the connector so as to provide an implanting force; and distally to impact the strike chamber so as to provide a removing force.

The use of a connector 112 that is distinct from the strike assembly 126 and that is separated from the strike assembly in a resting position enables the strike assembly to build up speed before imparting a force to the impactor. This build up of speed (and kinetic energy) is useable to deliver a large impact force (e.g., by the strike assembly rapidly decelerating upon impacting the connector). This enables an object to be implanted using a small number of impacts, which is beneficial for orthopaedic procedures since the use of a large number of impacts can reduce the fixation of an implant in a bone.

Furthermore, the spacing of the strike assembly 126 from the connector 112 enables a substantial impact energy to be provided using a low mass connector and/or strike assembly. The energy imparted to the connector by the strike assembly can be determined as $KE=\frac{1}{2}mV^2$, where m is the mass of the strike assembly and V is the speed of the strike assembly just before impact. Therefore, to provide a high energy impact there must be provided either a large mass or a large speed. It can be desirable to use a high mass and a low velocity for the strike impactor, since this can improve the fixation of the implant. Therefore, the strike assembly 126 may be arranged to:

- Weigh at least 0.6 kg, at least 1.2 kg, at least 1.8 kg, at least 2.5 kg, at least 4 kg, and/or at least 5 kg.
- Be capable of moving at least 1 m/s at the time of impact, at least 1.5 m/s, at least 2 m/s, at least 3 m/s, and/or at least 5 m/s.

With a weight of 4 kg and an impact velocity of 1 m/s, the strike assembly 126 is capable of imparting an impact energy of 2 J.

The use of a large mass for the connector 112 can reduce the fixation of an implant. Therefore, in some embodiments the connector weighs no more than 1 kg, no more than 0.5 kg, no more than 0.2 kg, and/or no more than 0.1 kg.

Typically, the strike assembly 126 is greater in mass than the connector 112. In some embodiments, the strike assembly has a mass that is at least twice that of the connector, at least three times that of the connector, at least five times that of the connector, and/or at least ten times that of the connector.

In order to achieve different weights, the strike assembly and the connector may comprise materials of different density. In particular, the strike assembly may comprise a material of greater density than the connector (e.g., twice the density, three times the density, five times the density, and/or ten times the density).

To provide appropriate space for the strike assembly 126 to build up speed, the connector 112 and the strike assembly are typically arranged so that the strike assembly (e.g., the proximal striker 108 of the strike assembly) is spaced by at least 3 mm, at least 5 mm, at least 10 mm and/or at least 20 mm from the connector in a resting position.

Similarly, the strike assembly (e.g., the distal striker 106 of the strike assembly) may be at least 3 mm, at least 5 mm, at least 10 mm and/or at least 20 mm from the connector (e.g., the rear of the strike chamber 110) in a resting position.

It will be appreciated that a similar build up of speed could be achieved without the connector 112—for example, the strike assembly 126 may be accelerated over a similar distance before directly impacting an object. However, directly impacting the object with the strike assembly can cause a less efficient transmission of force (since the strike assembly will rebound from the object). Using the connector, which can be substantially stationary at the time of impact (e.g., move less than 2 mm, less than 1 mm, and/or less than 0.5 mm), increases the efficiency of force transmission.

It will be appreciated that the use of a spaced strike assembly and connector, in particular where the strike assembly is substantially more massive than the connector, may be provided without the spool arrangement. For example, the spaced arrangement may be used with a gas powered or manually powered actuator mechanism.

Figure 3C:
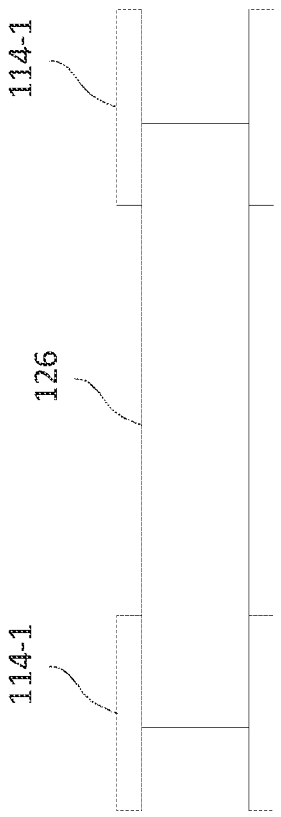

Referring to FIG. 3*c*, there is shown an embodiment of the actuator mechanism 100 that comprises a plurality of spools 114-1, 114-2. The plurality of spools may be provided either in series or in parallel. In particular, spools provided in series in differing locations along the strike assembly 126 may be used to provide differing forces. A first spool located distal relative to the strike assembly may be used to provide a removing force while a second spool located proximal relative to the strike assembly may be used to provide an implanting force. Furthermore, multiple spools may be used to provide a consistent force on the strike assembly by energising the spools in a ripple effect. Spools with different diameters (e.g., spools located in parallel) may be used to provide different magnitudes of force, where spools with small cross-sectional areas may be used to provide low impact forces and spools with large cross-sectional areas may be used to provide higher impact forces.

Embodiments that use a plurality of spools are described in more detail with reference to FIGS. 7, 8*a*, and 8*b*. In particular, FIG. 8*a* shows an embodiment with a plurality of parallel spools and FIG. 8*b* shows an embodiment with a plurality of spools located in series.

Figure 3D:
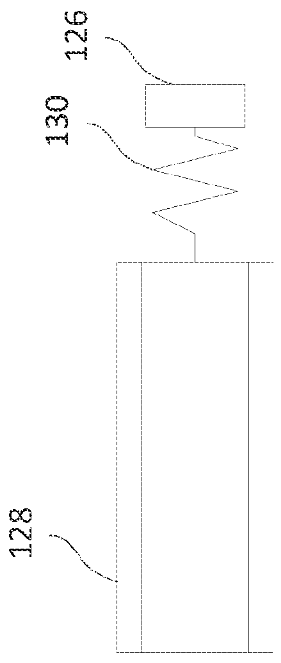

Referring to FIG. 3*d*, there is shown an embodiment of the actuator mechanism 100 that comprises an electromagnet 128. The electromagnet is typically formed of a ferrous, non-moving, core located within the spool 114. With this arrangement, the strike assembly 126 comprises a ferrous mass, which can be moved by a force generated by the electromagnet. The strike assembly may comprise a permanent magnet and/or a ferromagnetic material.

The electromagnet 128 can be used to provide either an implanting or a removing force by altering the direction of a current provided to the electromagnet.

As shown in FIG. 3*d*, in some embodiments, the actuator mechanism 100 comprises an energy storage mechanism such as a spring 130. In such embodiments, an energy can be stored in the spring by providing a current to the electromagnet. The current provided to the electromagnet can then be removed so that a force stored in the spring causes the strike assembly 126 to move so as to provide an impacting force. In such an embodiment, the spring is typically located between the electromagnet and the strike assembly.

This arrangement enables a single direction of current to be used to provide forces in either direction; e.g.:

- To provide an implanting force a current is provided that acts to force the strike assembly 126 away from the electromagnet 128 rapidly.
- To provide a removing force a current is provided that acts to slowly move the strike assembly away from the electromagnet, this current is then rapidly removed causing the spring to compress and move the strike assembly rapidly towards the electromagnet.

or

- To provide a removing force a current is provided that acts to force the strike assembly 126 towards from the electromagnet 128 rapidly.
- To provide an implanting force a current is provided that acts to slowly move the strike assembly towards from the electromagnet, this current is then rapidly removed causing the spring to extend and move the strike assembly rapidly towards the electromagnet.

The operation of an embodiment of the actuator mechanism is now described referring to FIG. 2, which shows the actuator mechanism in a resting position.

In this resting position the proximal striker 108 is spaced from the connector 112 within the strike chamber 110; the resting spring 122 is in a relaxed state; and no current is being provided by the power source 2 to the spool 114.

In order to provide an impacting force to drive an implant into the bone, a current is provided to the spool 114 from the power source 2. The properties of this current (e.g., the direction, the duration, and the magnitude) are determined by the control electronics 4 and depend on the primary input 6 and the secondary input 8 selected by the user.

The current supplied by the power source 2 to the spool 114 leads to the generation of a magnetic force that acts upon the ferromagnetic body 104 so as to move the body towards the active position (here the forwards position). As the body moves towards the forward position, the proximal striker 108 also moves in the proximal direction. Eventually, the proximal striker impacts the connector 112; this forces the connector forwards so that it impacts an implant. The acceleration of the body, and thus the impact force/energy, depends on the current that has been induced in the spool.

Furthermore, as the body 104 moves in the proximal direction, the return spring 122 is compressed and a compression force builds in the spring.

As the connector 112 moves proximally it impacts the implant. Following this, a rear surface of the connector impacts the bearing holder 116, which prevents further proximal movement of the connector. Once this position has been reached (or before this position has been reached), the current in the spool 114 is removed. Therefore, the magnetic force that is acting to move the body 104 to a proximal position is removed. This results in the compression force in the return spring 122 acting to move the body distally away from the proximal position to the resting position. Using the return spring, a consistent resting position can be achieved (e.g., where the return spring is in equilibrium) so that a consistent force can be applied using the connector.

In some embodiments, as the body 104 moves towards the resting position, the distal striker 106 contacts the rear of the strike chamber 110. This results in the strike chamber (and the affixed connector 112) moving in the distal direction (e.g., to return the connector to the resting position).

This process may be repeated a number of times in order to drive an implant into a bone.

While the above description with reference to FIG. 2 has considered the connector 112 moving so as to impact an implant, typically when an implant is being driven into a bone, the connector remains substantially stationary. In these embodiments, the connector may be fixed in place by the spacer 120, the bearing holder 116, a connection to the casing 102, and/or a force imparted by a user. In some embodiments, a holding structure or mechanism is provided on the casing (e.g., a protrusion from the casing), where this mechanism can be operated to prevent movement of the connector or removed to allow movement of the connector. As an example, a latch on the casing may be placed into a notch on the connector 112 to hold it in place, where this latch can be removed once an impacting procedure is completed. An implementation where the connector remains substantially stationary when providing a driving/implanting force to an implant is described below with reference to FIG. 4*a*.

Typically, a current is provided to the spool 114 for only a short period of time (for example for less than one second, less than 0.5 seconds, or less than 0.1 seconds). This results in a force being applied to the body 104 for only a short amount of time. The body is then able to rapidly move forwards and impact the connector before returning to the resting position under the influence of the return spring 122.

In order to remove an implant a similar process is used. Specifically, in order to provide an implanting force a current is provided to the spool 114 in a first direction; in order to provide a removing force a current is supplied in the opposite direction.

This results in the body 104 moving from the resting position to a distal position; the distal striker 106 also moves in the distal direction, eventually striking the rear side of the strike chamber 110. The strike chamber is connected to the connector 112 and so the impact of the distal striker acts to move the connector to a distal position so as to remove an implant from a bone. As the body moves towards the distal position, the return spring 122 extends.

As the strike chamber 110 and the connector 112 move distally, the rear side of the strike chamber eventually contacts the spacer 120 preventing further movement of the connector. At, or before, this point, the current to the spool is removed and the tensile force in the return spring 122 acts to return the body 104 to the resting position.

This process may be repeated a number of times in order to remove an implant from a bone.

By the impactor 1 having a resting position in between a proximal (e.g., implanting) position and a distal (e.g., removing) position, the impactor can be used to both attach and remove an implant from a bone. Typically, this involves providing current in a first direction to provide an implanting force and providing current in an opposite second direction to provide a removing force.

In some embodiments, the return spring 122 is alterable and/or interchangeable. By altering a property of the return spring (e.g., a resting tension placed on the return spring) the resting position of the strike assembly can be altered. This enables, for example, the impactor to be used with a distal resting position to provide an impacting force and a proximal resting position to provide a removing force. By altering the resting position, the distance between the strikers and the connector/strike chamber in the resting position can be maximised—this gives more space for the strike assembly to build up speed so as to provide high-energy impacts.

Another implementation of the impactor 1 is described with reference to FIGS. 4*a* and 4*b*. With this implementation, the connector 112 is arranged to be substantially stationary when the impactor is in use.

Figure 4A:
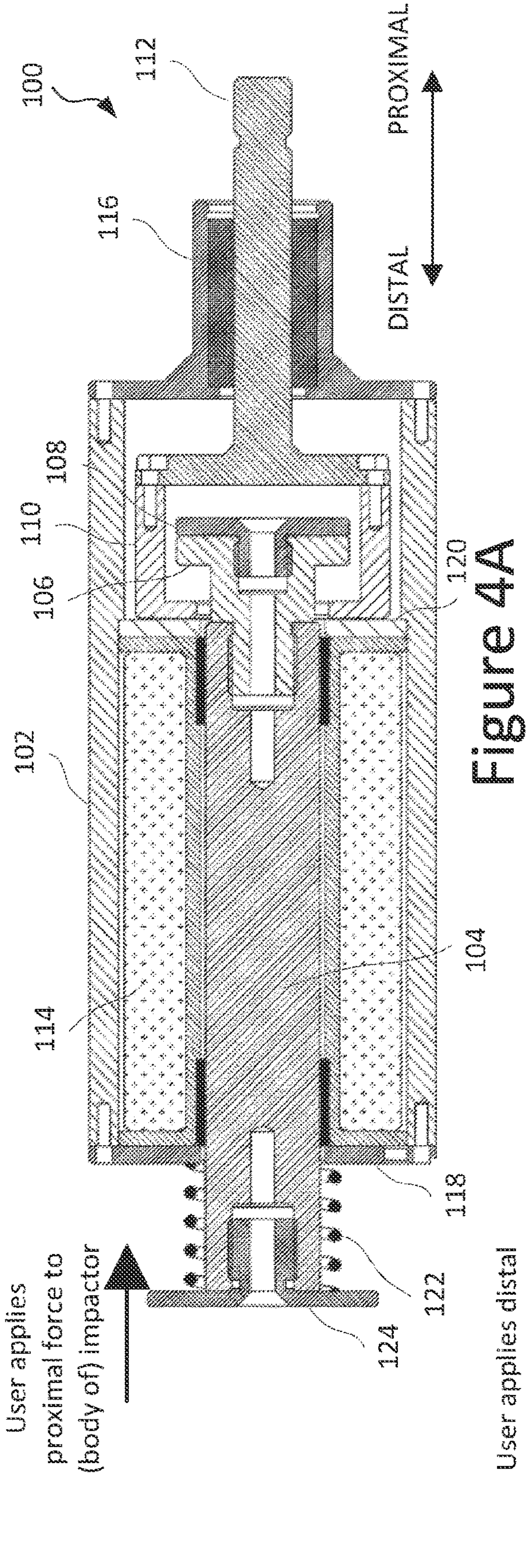
FIGS. 4*a*and 4*b* show positions of the actuator mechanism when the impactor is being used to, respectively, implant an implant and remove an implant.

Referring to FIG. 4*a*, when a user is attempting to implant an object that user is likely to provide a proximal force that acts to press the connector 112 into the implant. This results in a force being placed upon the connector when the impactor 1 is in the resting position (and the spool 114 is unpowered). This force results in the connector and the strike chamber 110 being forced in the distal direction so that when no current is applied to the spool the strike chamber comes to rest on the spacer 120 (as shown in FIG. 4*a*). The connector may then be fixed in place in this position (e.g., using a holding mechanism on the casing 102).

With the impactor in this resting position (and the strike chamber 110 resting on the spacer 120), the application of a current is provided to the spool. This current generates a magnetic field that acts on the strike assembly 126 and causes the strike assembly, and the proximal striker 108, to move in a proximal direction so as to impact the connector 112 and provide an implanting force to the object.

This movement also compresses the return spring 122 so that once the spool is no longer powered the return spring acts to move the striker assembly (and the proximal striker) away from the connector to the resting position. It will be appreciated that embodiments of the impactor 1 may be provided without the return spring. Another biasing mechanism may be provided; the strike assembly may be returned to the resting position by applying an appropriate force to the spool 114; and/or the user may manually move the strike assembly back to the resting position. The use of a biasing mechanism (e.g., the return spring) is beneficial since it provides a reliable way to consistently return the strike assembly to the resting position.

With this implementation, the connector 112 is typically substantially stationary, where the connector acts to transfer a force from the proximal striker 108 to an implant. The use of a moving strike assembly and a substantially stationary connector enables the provision of large impact forces, since the strike assembly 126 accelerates and builds up speed (and energy) over time before decelerating more quickly.

The strike chamber 110 resting on the spacer 120 in the resting position prevents the application of a distal force (e.g., as the strike assembly returns to a resting position) since the strike assembly remains spaced from the distal striker 106.

Typically, the return spring 122 is arranged so that in the resting position the body 104 is spaced from both the strike chamber 110 and the connector 112.

Figure 4B:
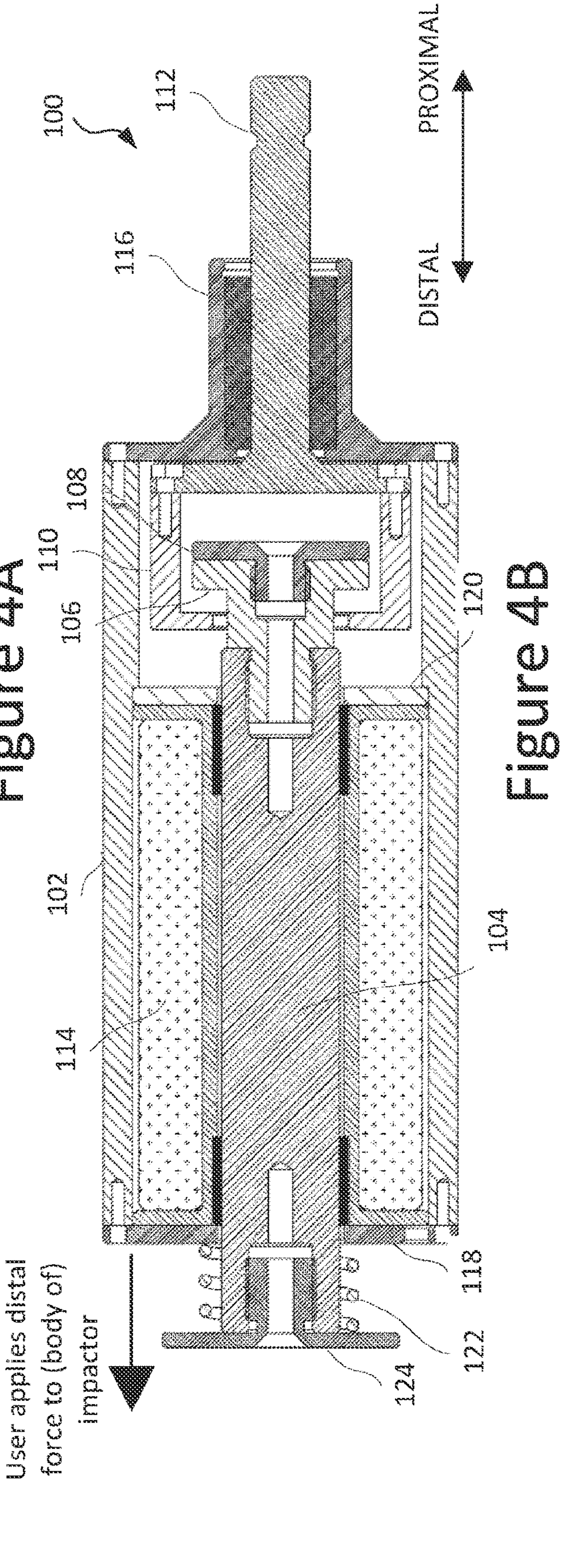

Referring to FIG. 4*b*, when the user is attempting to remove an object, the user is likely to provide a small distal force that acts to move the connector 112 away from the implant. This results in a force being placed upon the connector when the impactor 1 is in the resting position (and the spool 114 is unpowered). This force results in the connector and the strike chamber 110 being forced in the proximal direction so that when no spool current is applied the connector typically comes to rest on the bearing holder 116. The application of an appropriate current to the spool then causes the distal striker 106 to move in a distal direction to impact the strike chamber to impart a removing force to the connector. The strike assembly and the body 104 then return to the resting position under the force of the return spring 122.

The impactor 1 can also be provided with a single driving direction that is used for both implanting and removing implants. In an embodiment of the impactor, the implanting process works as described above, where a force is applied to the spool 114 that acts to move the body 104 in a proximal direction.

As explained above, in order to remove an implant, the power source 2 may supply a current that acts to move the body in the distal direction.

Alternatively, in order to remove an implant, the power source 2 may supply a current that acts to move the body 104 towards the proximal position. When a user is attempting to remove an implant, they place a distal force on the impactor (forcing the impactor away from the implant). This results in the connector 112 moving in the proximal direction until it abuts the bearing holder 116. When a force is applied to move the body, the body moves towards the forward position; however, before the proximal striker 108 can contact the connector, the movement of the body (and the proximal striker) is halted by the compression of the return spring 122.

This compression causes the body to move the towards the backwards position (in a distal direction). The distal striker 106 also moves backwards, eventually impacting the strike chamber 110, which causes the connector to move in a distal direction and to apply a removal force to an implant. In this way, both driving and removal forces can be applied using currents with the same direction. Furthermore, both driving and removal forces can be provided using a non-permanent magnet for the body. This design also reduces the range of travel required for the body; by moving the starting position of the connector, the body moving through a fixed range of travel can be used to either drive or remove an implant. In other words, if an initial proximal force is placed on the impactor, the movement of the body acts to drive an implant; if an initial distal force is placed on the impactor the same movement of the body acts to remove an implant.

Equally, and referring again to FIG. 4*b*, in order to provide a removing force, the spool 114 may be powered in the resting position and unpowered in the active position, where the strike assembly 126 exerts a force on the connector 112 after a current is removed from the spool.

In particular, the spool 114 may receive a current in the resting position, which current results in the generation of a magnetic field that acts to move the strike assembly 126 to a proximal position (e.g., so that in a resting position, the connector 112 rests against the rear surface of the linear bearing 116). In this position, the return spring 122 is compressed; the strike assembly is then held in place by matching forces provided by the spool and the return spring (and, optionally, a user, who may be applying a distal force).

Typically, the spool is arranged to receive a gradually increasing current so as to move the strike assembly 126 slowly towards the proximal resting position and to avoid the provision of an undesirable implanting force.

When the user is ready to provide a removing force to an object, the current being provided to the spool 114 is removed; the strike assembly (and body 104) then moves in the distal direction due to the compression force in the return spring 122. This causes the distal striker 106 to move in the distal direction until it strikes the strike chamber 110. This provides a removal force to the connector 112 that acts to remove an implant.

In this way, a current acting to move the strike assembly in the proximal direction can be used to provide a distal force.

Another current may then be provided to the spool 114 and the process may be repeated to provide multiple impacts.

The above-described implementation, where driving and removing forces are provided using the same direction of movement of the body 104 and the strike assembly can be of particular relevance where a non-permanent magnet is used for the body. In such embodiments, a current induced in the body (and a resultant magnetic field) may act to oppose a magnetic field generated by a current in the spool. Therefore, altering the direction of current will not alter the direction of movement of the body (since switching the direction of current in the spool will simply switch the direction of the current induced in the body).

Typically, in order to provide the implanting force a large current is rapidly provided to the spool 114. This places a large instantaneous force on the strike assembly 126 so that it quickly moves in the proximal direction. Typically, in order to provide the removal force, a current is gradually provided to the spool. In this way, the strike assembly moves slowly in the proximal direction and the return spring 122 is slowly compressed. The current is then removed quickly (or instantaneously) so that the compressive forces in the return spring act to move the strike assembly quickly in the distal direction.

In the above examples, the return spring 122 is used to provide a removal force when a current provided to the spool 114 is removed. It will be appreciated that the return spring could equally be used to provide a driving/implanting force. For example, the strike assembly 126 may be arranged such that a current provided to the spool acts to move the strike assembly in a distal direction (e.g., the body 104 may be provided proximally to the spool in a resting position). Therefore, when the spool is powered, the strike assembly moves to a distal position and the return spring is extended. The removal of this power to the spool causes the strike assembly to move forward so as to provide an implanting force to the connector 112.

Similarly, a removing force may be provided using the provision of current to the spool 14. In particular, the strike assembly 126 may be arranged such that a current provided to the spool acts to move the strike assembly in a distal direction (e.g., where the body may be provided distally to the body 104 in a resting position). Therefore, the provision of a current to the spool will act to move the strike assembly (and the distal striker 106) in the distal direction leading to the distal striker impacting the strike chamber 110 and the connector moving in the distal direction so as to provide a removing force.

In some embodiments, the impactor 1 is arranged to acquire data relating to the impact; for example, the impactor may determine an impact force, impact energy, or implant stability. Data may be acquired by monitoring a current induced in the spool 114 by the body 104 after the body strikes the connector. The return of the body from a forwards position to a resting position will induce a current in the spool 114. The properties of this current (e.g., the magnitude and duration of the current) can be used to determine the properties of the impact. Equally, sensors (e.g., accelerometers) may be used to determine an impact speed, impact frequency, or impact resistance. The data acquired by the impactor 1 is typically presented to the user of the impactor via the screen 10. The data may also, or alternatively, be transmitted to an external device (e.g., following use) so that implant procedures can be analysed.

In some embodiments, the connector 112 comprises one or more sensors, such as a load cell, an accelerometer, and/or a strain gauge. The sensors are arranged to acquire impact data, typically the sensors are arranged to measure an impact energy, an impact force, and/or an implant stability.

The impact parameters, e.g., the impact force, may be altered based on determined impact properties. As an example, if a first impact is determined to have an undesirably low impact force or undesirably low penetration, a subsequent impact may be performed using a higher impact force (e.g., a higher spool current). Properties of the patient's bones, such as bone density, may affect the impact procedure so that the same impact energy used for different patients might result in substantially different impact forces being provided. Therefore, typically the impactor is arranged to determine properties of the object and/or a patient from a first impact and used to adjust the impact energy and/or force for future impacts. This adjustment typically uses a closed control loop and/or a proportional-integral-derivative (PID) controller to adjust impact force. Specifically, the user inputs desired parameters (e.g., impact force) via the inputs 6, 8; an impact is then delivered and measured; and the measured properties are used to alter features of the current delivered to the spool 114 for subsequent impacts.

The impactor 1 is typically arranged such that a user can alter, or input, one or more of:

- An impact energy. A selected impact energy can be provided by providing a suitable current to the spool 114.
- An impact force. The impact force typically depends on both the impact energy and the object being impacted. Therefore, a desired impact force is typically provided by applying a first impact at a first impact energy, determining the difference between a determined (e.g. measured) impact force and the desired impact force, and providing a second impact at an appropriately altered impact energy (e.g. if the determined impact force is 20% less than the desired impact force the second impact may be arranged to have an impact energy 20% greater than the first impact).
- A desired implant stability. The stability may be determined by measuring, for example, by applying a force to an implant and detecting the resistance of the implant to movement.

In some embodiments, the control electronics 4 is arranged to receive information about a use, for example the control electronics may receive information about the object being implanted (e.g., a material and/or density of the object) and/or information about the surface into which the object is being implanted (e.g., a bone density and/or patient age). This information may be used by the control electronics 4 to determine appropriate impact properties, such as an appropriate impact energy and/or force.

Methods of Operation

Figure 5:
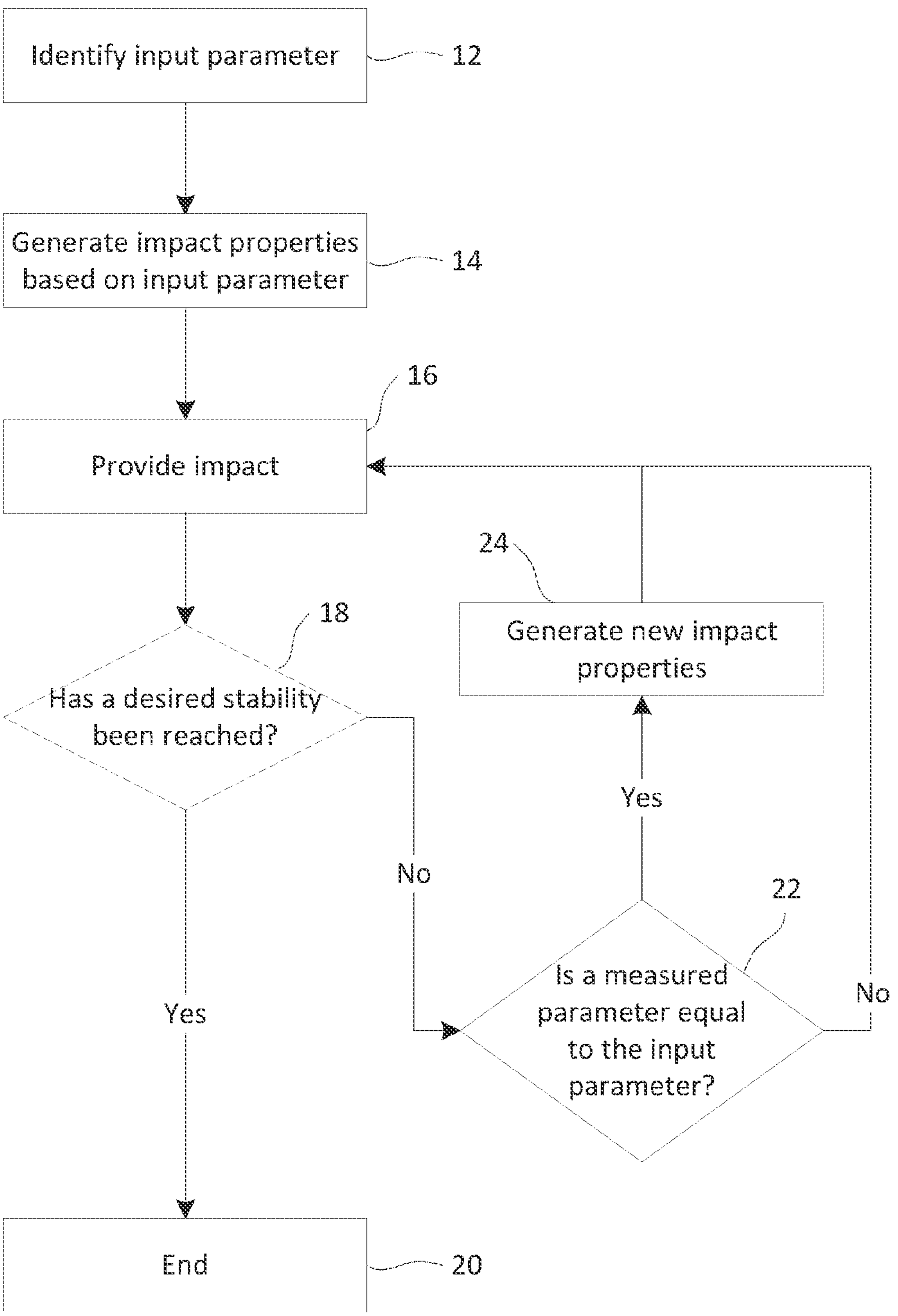
FIG. 5 shows a method of providing impacts in dependence on an input parameter.

Referring to FIG. 5, there is shown a method of implanting an object using a control system. Such a method may be performed by the control electronics 4 of the impactor 1.

In a first step 12, the control electronics 4 identifies an input parameter (or a plurality of input parameters). Typically, this parameter is entered by a user (e.g., using the first input 6 and/or the second input 8), where this parameter may comprise a desired stability, a desired impact energy, and/or a desired impact force.

In a second step 14, the control electronics 4 generates impact properties based on the input parameter. Typically, this comprises determining a suitable current that can be provided to the spool 114 to achieve an impact with the desired input parameter. This may comprise determining a suitable impact energy and then determining a current profile that relates to this impact energy. The relationship between the current and the energy is typically dependent on the properties of the strike assembly 126 as well as the properties of the spool 114.

The energy transferred to the spool may be determined using the relationship $$E = \frac{1}{2}LI^2$$

(where L is the inductance in Henrys and I is the current in Amperes). The energy density of the generated magnetic field may then be determined using the relationship $$u_B = \frac{lI^2}{Al}$$

(where A is the cross-sectional area of the spool and I is the length of the spool). These equations may be used to determine an appropriate current for the spool 114.

Since the produced values may differ from the calculated values (e.g., due to manufacturing tolerances, resistances in the components of the impactor 1, heat losses etc.) the control electronics 4 may be arranged to perform a calibration process. This calibration process typically comprises determining a relationship between an input current and a resultant impact energy, where the calibration may use data from test procedures and/or previous impacting procedures.

Typically, the impact properties generated based on the input parameter are arranged to provide a first impact with an impact energy that is lower than an impact energy calculated in relation to the input parameters. In this way if the actual impact energy is greater than calculated impact energy there remains a small risk of causing a fracture.

As has been described above, providing a removing force may comprise removing a current from the spool 114. In these cases, the force on the strike assembly 126 that acts to move the strike assembly towards the strike chamber 110/connector 112 is typically provided by the return spring 122. Specifically, a compressive force in the return spring acts to move the body 104 once a magnetic force placed on the body by the spool is removed. In this instance, the force of the impact, and the impact energy, can still be controlled by controlling the flow of current to the spool so as to control the compression of the spring.

The energy in the return spring 122 can be calculated using the equation $$E = \frac{1}{2}kx^2,$$

where k is a spring constant and x is a displacement from an unstretched position. The spring constant is typically measured before an impacting procedure and provided to the control electronics. The displacement may be measured using, e.g., a strain gauge. Equally, the energy in the return spring can be calculated using the equation E=Fx. Here the force in the return spring can be determined by determining the force that must be placed on the strike assembly (by the spool 114) in order to hold the return spring in a certain position. Therefore, a current provided to the spool the spool (which is related to the force placed on the body 104 by the spool) can be used to determine an energy stored in the return spring and a compressive force of the return spring.

In a third step 16, an impact is provided based on the impact properties. Providing an impact typically comprises providing a current to the spool 114. As has been described above, providing a removing force may comprise removing a current from the spool.

In a fourth step 18, it is determined whether a desired stability has been reached. This determination may be made by the control electronics 4 or by a user of the impactor 1. For example, a small current may be provided to the spool 114 and a resulting movement (or lack of movement) of the implant may then be detected by a sensor of the impactor.

In a fifth step 20, if the desired stability has been reached, the impacting process ends. This determination may be made by the control electronics 4 and/or by a user of the impactor 1.

In a sixth step 22, if the desired stability has not been reached, the control electronics 4 determines whether a measured parameter of the impact is equal to the input parameter. For example, the control electronics may compare a measure impact energy to an input impact energy and/or a measured impact force to an input impact force. A comparison may be made for multiple parameters.

If the measured parameter is in accordance with the input parameter, the method returns to the third step 16 and another impact is provided based on the previously generated impact properties. This impact may occur automatically, so that a user starts an impacting process and then does not need to take any further action (e.g., multiple impacts may occur without further action); alternatively, each impact may require user input, e.g., depressing a trigger.

If the measured parameter is not in accordance with the input parameter, then in a seventh step 24, the control electronics 4 generates new impact properties. These new impact properties typically comprise a modification of the previous impact properties. For example, if the measured impact force was lower than the input impact force, the previously provided current is increased. The magnitude of the change in impact properties typically depends on the discrepancy between measured and input parameter, e.g., the properties may be changed proportionally to a percentage difference (so a 20% shortfall in impact force results in a 20% increase in current).

The third step 16, fourth step 18, fifth step 20 and sixth step 22 are then repeated until a desired stability is achieved and/or until the user halts the process.

Data collected during use can be used to alter the operation of the impactor 1 for a single situation (e.g., a single THA procedure) or for a range of situations (e.g., future THA procedures). In particular, the current supplied by the power source 2 to the actuator mechanism 100 may be dependent on properties determined from impacts from previous uses. This enables a desired impact energy to be provided across the lifetime of the impactor, where the current needed for a given impact energy may change with time (e.g., as the power source 2 degrades). By considering previous uses, the required changes can be continuously reviewed. The impact properties may also depend on a user of the impactor, where different users may apply different initial forces and/or have different preferences. Therefore, typically, the control electronics 4 is arranged to determine a user of the impactor, e.g., by enabling a user to log in to the impactor.

In particular, data collected during use relating an impact energy and/or impact force to an impact stability may be used to determine appropriate impact energies for future procedures.

The determination of beneficial impact energies—and, for example, whether it is preferable to use a large number of low force impacts or a smaller number of higher force impacts in a given situation or whether it is preferable to use a large current provided for a short time or a smaller current provided for a longer time—may depend on artificial intelligence and/or machine learning.

Data collected during use may also be analysed to determine features of procedures (e.g., to determine a success rate and/or to analyse any problems that arose). In some embodiments, this involves data collected during surgeries being transmitted to an external server (e.g., via a USB cable or via an area network connection).

Figure 6A:
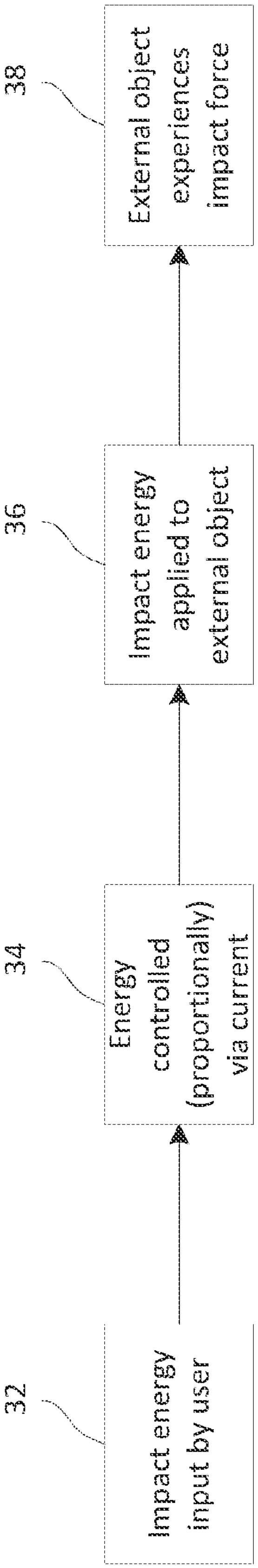
FIGS. 6*a* and 6*b* show, respectively, open-loop and closed-loop control systems for determining a current to supply to a spool.
Figure 6B:
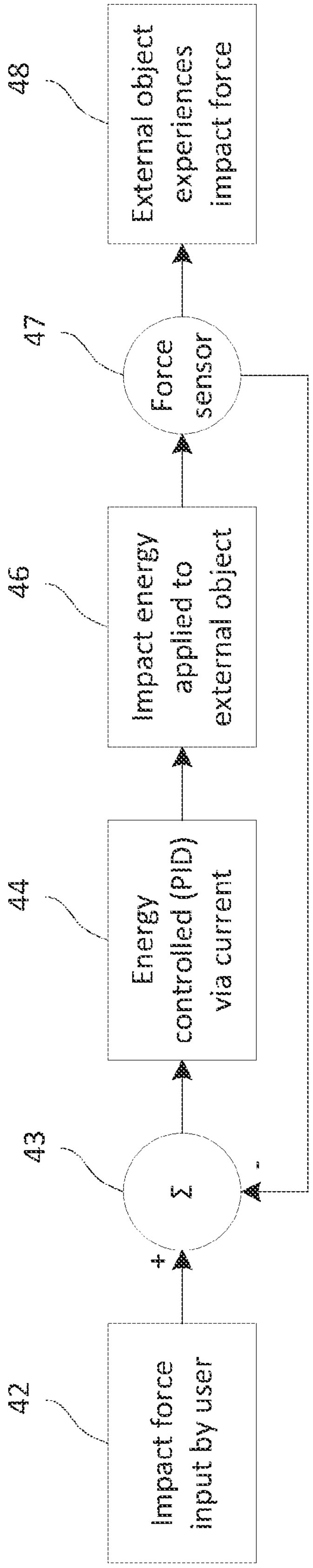

Referring to FIGS. 6*a* and 6*b*, two alternative control systems for providing energy to the spool 114 (and therefore the strike assembly 126 and the connector 112) are described. The control electronics 4 may implement either, or both, of these control systems, where a user may be able to select a control system to use.

Referring to FIG. 6*a*, an open-loop control system is described.

In a first step 32, the user inputs an impact energy.

In a second step 34, the control electronics 4 determines a current to provide to the spool 114 based on this input energy. Determining the current typically comprises determining a magnitude and/or a duration of current to provide to the spool. The determination of the current is typically based on a table, graph, or equation. Normally, the impact energy is proportional to the magnitude/duration of the current provided to the spool.

In a third step 36, an impact energy is applied to an external object as has been previously described. In particular, the power source 2 provides the determined current to the spool 114. This current results in the generation of a magnetic field, which magnetic field moves the strike assembly 126 so that it impacts the connector 112, which connector then impacts the object.

In a fourth step 38, the external object experiences a force that depends on the applied impact energy. The impact force is typically proportional to the impact energy; however, this force also depends on other factors such as the material of an implant and the hardness of a bone into which an implant is being inserted.

In this regard, impact force (as opposed to impact energy) is typically the key factor in bone fracture during implant seating. The impact force—and in particular the peak impact force—provided to the implant is dependent upon the impact energy (and thereby on the energy provided to the spool 114). However, the relationship between the impact energy and the impact force is not always straightforward since it depends on several factors, for example:

- Geometry (e.g., the geometry of the implant/rasp/impactor).
- Stiffness/damping of impacting bodies (e.g., the stiffness of the implant/rasp/impactor)
- Stiffness/damping properties of the material supporting the impacting bodies (e.g., the stiffness of the bone and soft tissue surrounding the implant/rasp)

Lower stiffnesses tend to lead to lower impact forces since the impact energy is provided to the implant over a greater duration. In other words, where the components of the impactor are able to deform the impactor will provide a comparatively low force over a comparatively high duration (as compared to an impactor with stiffer components).

Not least because this relationship depends on variables external to the impactor 1 (e.g., bone stiffness), it is not straightforward to determine a relationship between an impact energy and an impact force—and so it is not straightforward to determine a relationship between a current/energy provided to the spool 114 and an impact force.

Therefore, with the open loop system described with reference to FIG. 6*a* it can be difficult to provide an optimal impact force.

Referring to FIG. 6*b*, the control electronics 4 may provide a closed loop system.

In a first step 42, the user inputs an impact force (as opposed to an impact energy).

In a second step 44, the control electronics 4 determines a current to provide to the spool 114 based on this input energy. The determination of the energy typically depends on a proportional-integral-derivative (PID) controller as has been described with reference to FIG. 5.

In a third step 46, an impact energy is applied to an external object and in a fourth step 48, the external object experiences a force that depends on the impact energy.

With the closed loop system, there is provided a sensing step 47 in which the force being applied to the external object is measured by a force sensor. This force sensor typically comprises a force sensor located along the impact path (e.g., proximally to the impact chamber and/or integrated into the connector 112) so that the force sensor is able to measure the output impact force. More specifically, the force sensor is able to determine a difference between an expected impact force (which may be determined based on an equation that relates a spool energy to an impact force) and an actual impact force.

With the closed loop system, there is also provided a feedback step 43 such that the second step 44 of determining an impact energy for a second impact is dependent on the output of the force sensing step 47 and is thereby dependent on the actual impact force detected by the force sensor for a first impact.

The use of this closed loop system enables variables such as bone hardness and implant material to be accounted for by the control electronics 4.

To avoid inadvertently providing an excessive impact force with the first impact (before the force sensor has the opportunity to determine a relationship between impact energy and impact scheme, the impactor is typically arranged to provide a low energy impact as the first impact and to thereafter increase the impact energy in order to meet, but not significantly overshoot the input force. The ramp up from the first impact to the desired impact (where it is expected that the desired input force will be provided) typically comprises only a small number of ramp up impacts (e.g., no more than five and/or no more than three ramp up impacts). In other words, the impactor may provide a first impact, and/or a plurality of first impacts, with an impact force that is lower than a desired impact force and may then determine a desired impact energy based on this first impact, which desired impact energy is associated with the desired impact force.

In some embodiments where the control loop is sufficiently reactive, the control electronics 4 is able to influence impact force during an impact—removing the need for multiple 'ramp up' hits. Specifically, the control electronics may be able to determine at the beginning of an impact whether the impact force being provided is greater than or less than the expected impact force and may alter the current provided to the spool while the impact is ongoing.

Sensing

In order to provide consistent and desired forces, it is desirable to measure a variety of operational parameters, such as the location of the strike assembly 126 and the force applied to the object by the connector 112.

These parameters may be measured using various sensors, for example there may be provided a position sensor that detects a position of the strike assembly 126 and a separate force sensor that detects a force applied by the connector 112.

In some embodiments, the spool 114 is used as a sensor, so that one or more operational parameters are determined in dependence in the spool. In this regard, the movement of the strike assembly 126 induces a current in the spool that opposes the current provided by the power source 2 (e.g., via a back electromagnetic force, or back emf). The magnitude and duration of this induced current can be used to determine a number of operational parameters.

More specifically, the spool 114 can be modelled as an inductor and resistor in series. The properties of this inductor and resistor circuit—and in particular the current to voltage relationship of the circuit, can be used to determine operational parameters.

Exemplary operational parameters that may be determined in dependence on a current and/or voltage in the spool 114 include:

Solenoid Resistance (e.g., Spool Resistance):

- By applying a voltage/current from the power source 2 to the spool 114 and then measuring the resultant voltage/current in the spool, the spool resistance can be established via Ohms law $$\left(R = \frac{V}{I}\right).$$

Typically, readings of the current and voltage are taken over several hundred milliseconds to mitigate the transient impedance of the spool inductor.

Temperature:

- The resistivity (ρ) of the spool 114 is a function of the temperature of the spool. By measuring the spool resistance (R), and with use of the mechanical parameters of the spool (spool length ($\ell$) and spool cross-sectional area (A)), the spool resistivity can be calculated using the equation $$\rho = \frac{\ell \cdot A}{R}.$$

The resistivity can then be searched in a look-up table to find the temperature of the spool.

Position:

- The inductance of the spool 114 is a function of the displacement of the strike assembly 126 relative to the spool. By monitoring the current flowing through the spool when the spool is powered and accounting for the spool resistance (e.g., via the above methods), the inductance of the spool can be calculated. This inductance can then be searched on a look-up table to find the position of the strike assembly 126. This method may be used to ensure that the strike assembly is located in the same position before each impact—and this helps to ensure that the impactor 1 provides consistent impact forces.

Mechanical Load:

Energising the spool 114 causes the striker assembly 126 to move relative to the spool (as described above). When the strike assembly encounters resistance (due to impacting the connector 112, which connector impacts an object), the strike assembly decelerates, and this deceleration results in the generation of a back emf across the solenoid. By monitoring the profile of this back emf, the mechanical load on the strike assembly—and thus the impact force provided to the object—can be calculated. This enables the spool to be used as a force sensor.

The use of the spool reduces the number of components required in the impactor 1 and so enables the provision of a compact impactor. Furthermore, since the spool is already connected to the control electronics 4, the variables measured using the spool can be recorded, output, and/or transmitted with minimal further processing.

Multiple Spools

Figure 7A:
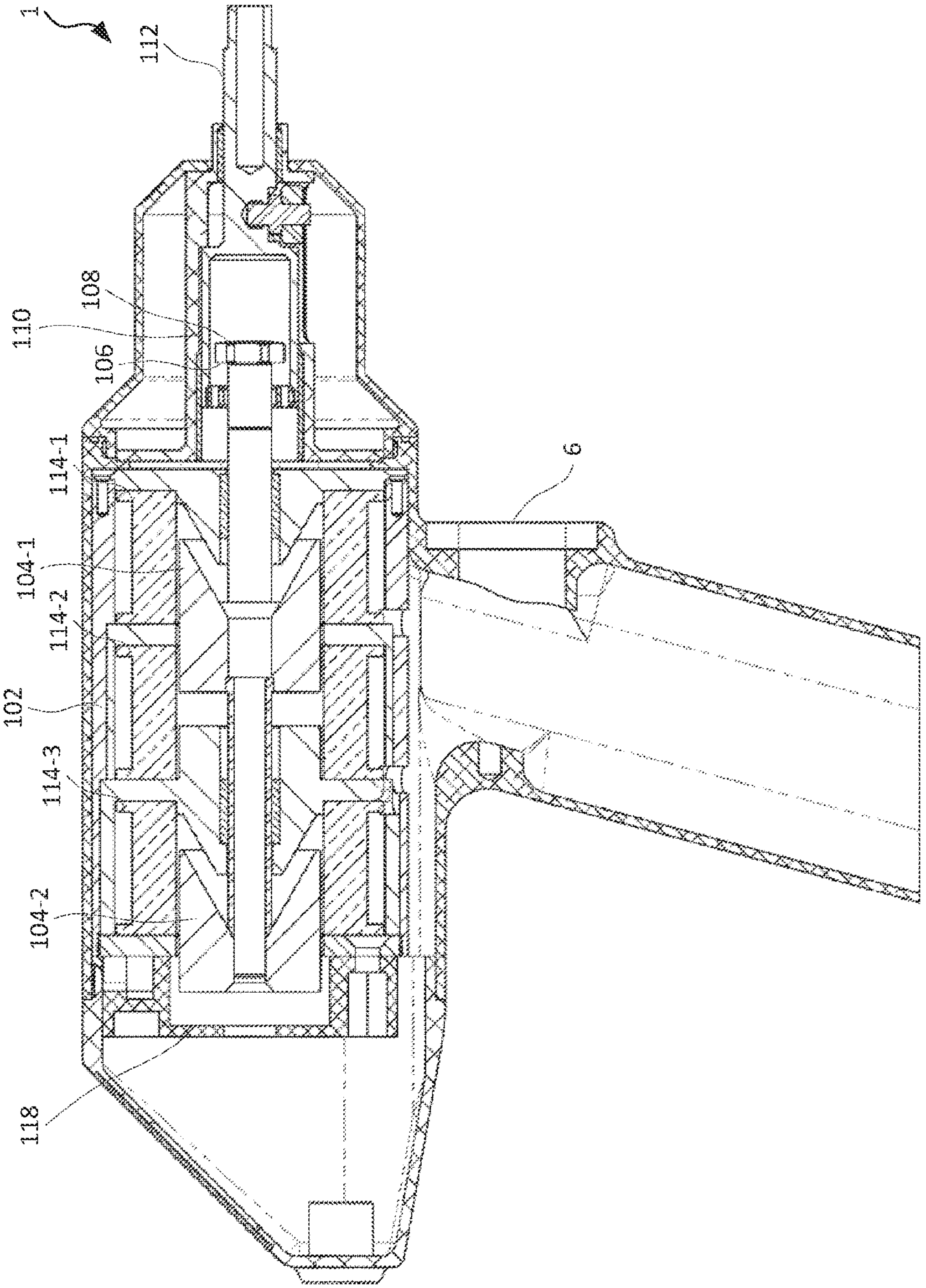
FIGS. 7*a* and 7*b* show another embodiment of the actuator mechanism.
Figure 7B:
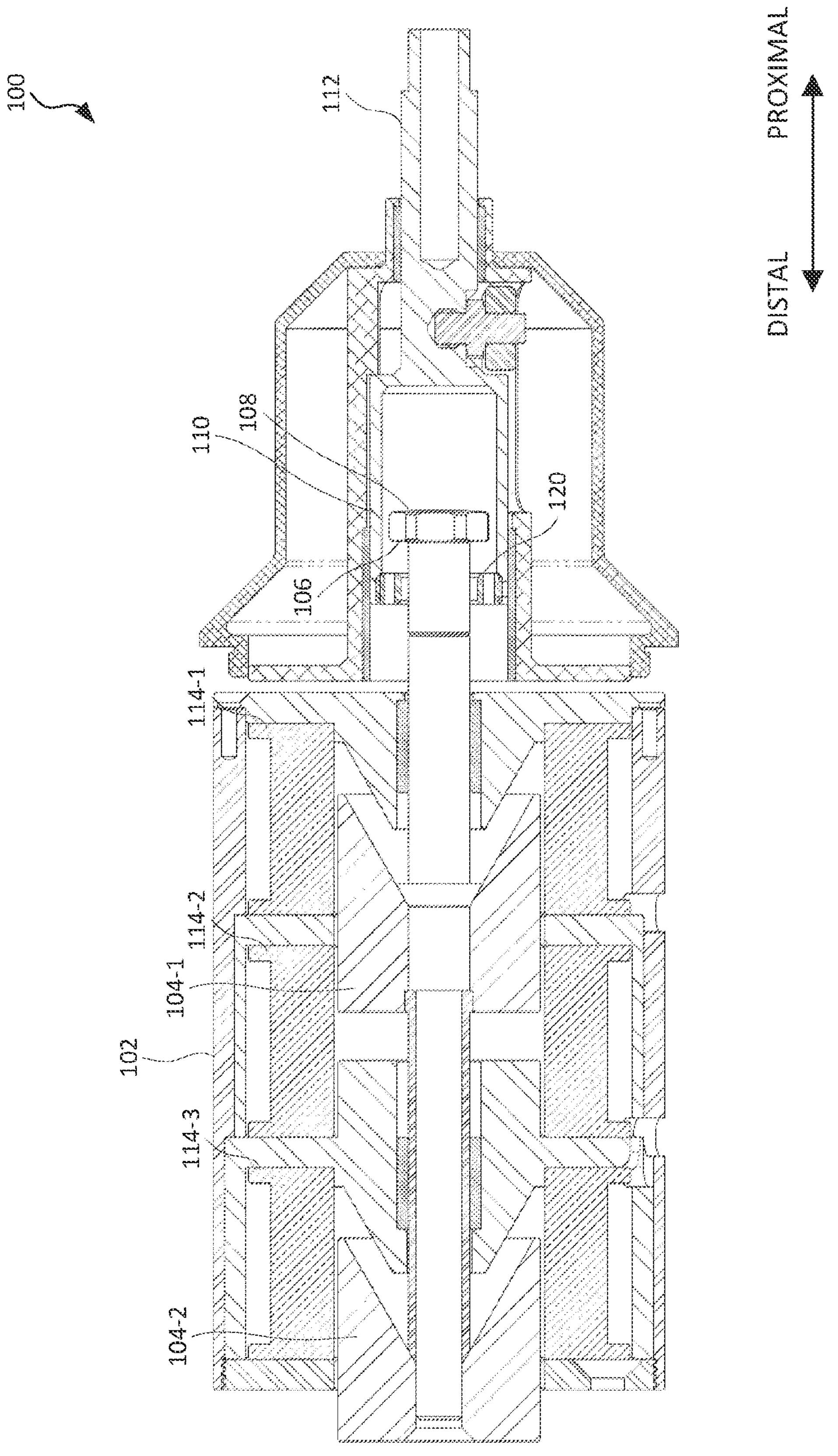
Figure 8A:
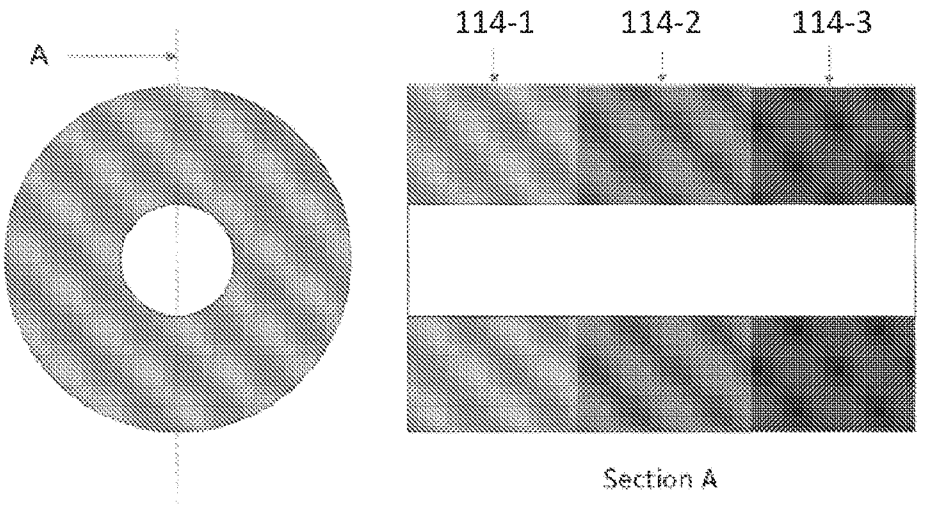
FIGS. 8*a* and 8*b* show arrangements of spools in the impactor.
Figure 8B:
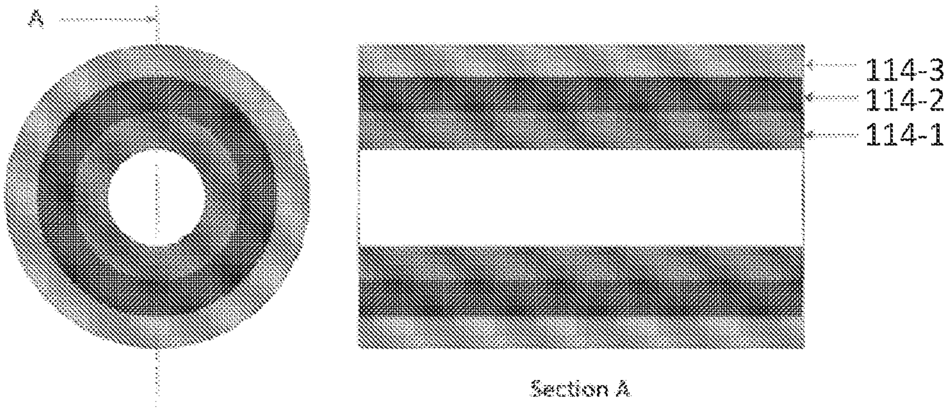

Referring to FIGS. 7*a* and 7*b*, and as has been described previously with reference to FIG. 3*c*, in some embodiments the impactor 1 (and more specifically the actuation mechanism 100) comprises a plurality of spools. This can be considered to be the impactor comprising a spool 114, which spool is formed of a plurality of component spools 114-1, 114-2, 114-3.

Specifically, the impactor 1 of FIGS. 7*a* and 7*b* comprises two proximal impact spools 114-1, 114-3 and one distal impact spool 114-2.

The proximal impact spools 114-1, 114-3 are arranged so that the provision of current to the proximal impact spools results in a magnetic field that moves the strike assembly 126 in the proximal direction.

The distal impact spool 114-2 is arranged so that the provision of current to the distal impact spool results in a magnetic field that moves the strike assembly 126 in the distal direction.

In practice, this typically comprises the proximal impact spools 114-1, 114-3 and the distal impact spool 114-2 comprising wire that is wrapped around the body 104 in different directions.

Typically, the forces required to remove an implant are lower than the forces required to insert an implant, therefore the impactor 1 may be arranged to provide a maximum proximal force that is greater than a maximum distal force that the impactor is able to provide. This is reflected in the layout of the impactor. The number of proximal impact spools may be greater than the number of distal impact spools. More generally, the total volume, total surface area and/or total length of the proximal impact spools may be greater than the total surface area and/or total length of the distal impact spools.

While the embodiment of FIG. 7 has two proximal impact spools 114-1, 114-3 and one distal impact spool 114-2, more generally the impactor 1 may comprise a plurality of component spools including one or more proximal impact spools and/or one or more distal impact spools. The impactor may comprise a plurality of proximal impact spools and/or a plurality of distal impact spools. Typically, the impactor comprises a greater number of proximal impact spools than distal impact spools.

The use of differing numbers/surface areas of component spools enables the provision of appropriate proximal forces and distal forces while minimising the weight of the impactor 100.

The strike assembly 126 may similarly comprise a plurality of component bodies and/or a plurality of component strikers. Such an arrangement is useable to minimise the stroke length of the strike assembly and to provide a compact impactor (where each of the component bodies impacts a different part of the connector). Each component body may be arranged in dependence on a corresponding component spool.

Each of the component spools 114-1, 114-2, 114-3 may have a different length (or there may be provided a single proximal impact spool that is longer than a single distal impact spool).

Typically, the spools are arranged in an alternating arrangement, e.g., in FIG. 7 the distal impact spool 114-2 is located between the proximal impact spools 114-1, 114-3. More generally, the spools may be arranged so that the proximal impact spool(s) and the distal impact spool(s) are each located axially symmetrically about a location of (e.g., the centre of) the body 104 and/or the strike assembly 126. This provides an impactor that has comparable proximal and distal strokes.

Referring to FIGS. 8*a* and 8*b*, two possible arrangements of the component spools 114-1, 114-2, 114-3 are shown.

Referring to FIG. 8*a*, there is shown a series arrangement of the component spools 114-1, 114-2, 114-3. This arrangement provides a plurality of spools located adjacent each other in the axial direction.

Referring to FIG. 8*b*, there is shown a parallel arrangement of the component spools 114-1, 114-2, 114-3. This arrangement provides a plurality of spools located adjacent each other in the radial direction.

In each of these arrangements, the distal impact spool 114-2 is arranged between the proximal impact spools 114-1, 114-3. While an alternating arrangement is typical in embodiments with a plurality of component spools, it will be appreciated that this alternating arrangement is not necessary.

A combination of series and parallel arrangements may be provided. Furthermore, a multistrand arrangement may be provided, where the component spools 114-1, 114-2, 114-3 overlap.

Current Profile

Typically, the spool 114 is operated in dependence on a semiconductor device, e.g., a transistor, where the supply of current to the spool is dependent on the semiconductor. In particular, the spool may be operated in dependence on a metal oxide semiconductor field effect transistor (MOSFET).

Figure 9A:
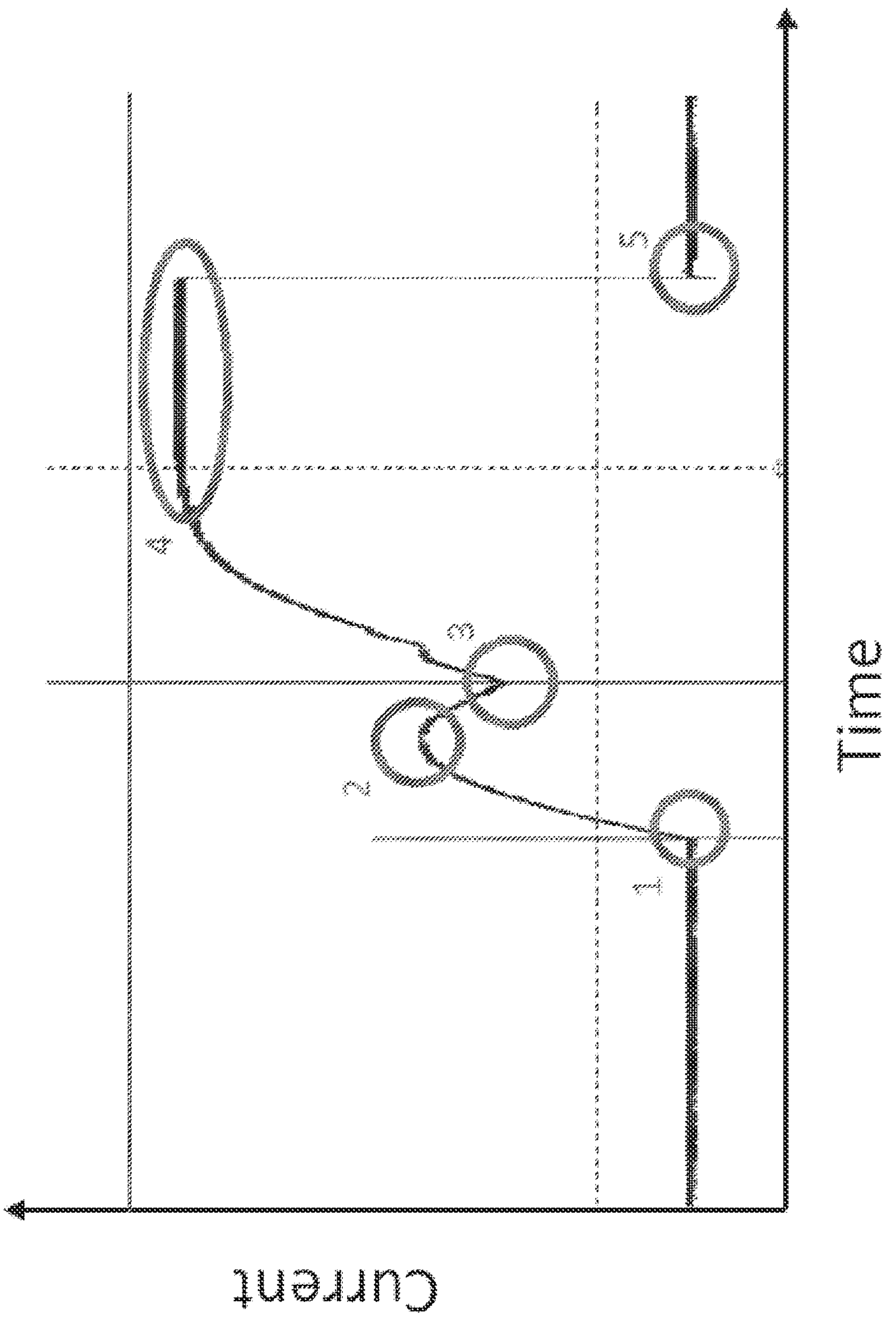
FIGS. 9*a* to 9*d* illustrate methods of powering the spool(s).

Referring to FIG. 9*a*, there is shown a typical operating profile for the spool 114 when a semiconductor is used to control the flow of current into the spool.

There are five critical points on this operating profile:

1. A current is supplied to the spool 114 by the power source 2. The current in the spool induces a magnetic field, which acts to move the strike assembly 126.
2. The strike assembly 126 encounters some resistance (for example, the strike assembly may strike the connector 112)—this leads to the induction of a back emf, which causes a reduction in the current in the spool 114.
3. The strike assembly 126 reaches its maximum proximal or distal position and so the impactor 1 stops providing energy to the object (and the back emf stops being induced).

4. The current reaches a maximum steady state current (this maximum current depends on the resistance/inductance of the spool 114).
5. The power source 2 ceases providing the current to the spool 114.

As seen by this profile, the spool 114 may not reach its maximum current until after the impact has occurred. When the impact occurs before the spool reaches its maximum current, only a small impact force can be achieved (as compared to when the impact occurs after the spool reaches its maximum current).

Figure 9B:
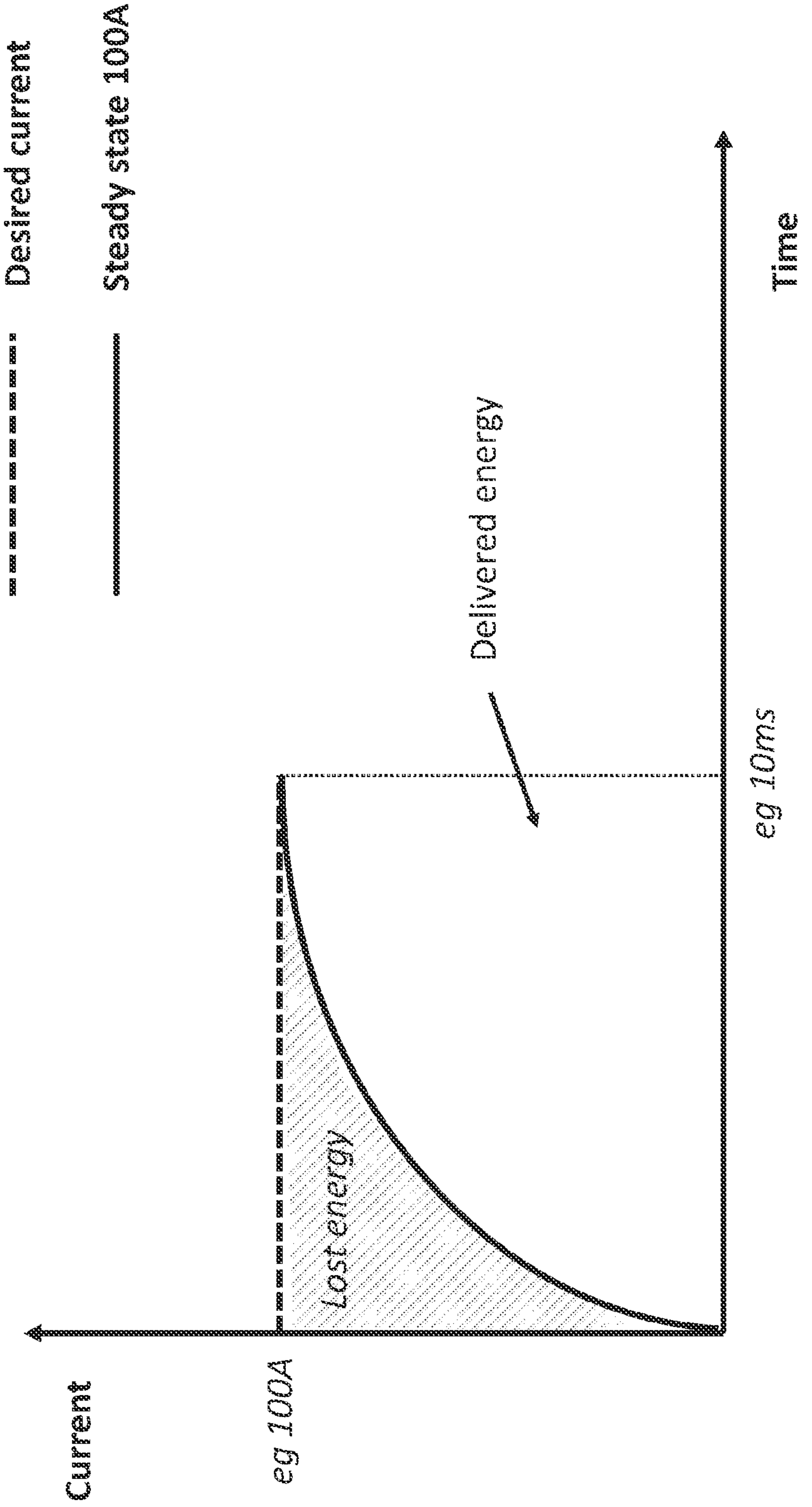

Referring to FIG. 9*b*, such a situation (where the spool does not reach its maximum current) is common when the power source 2 is arranged to aim for a target current (e.g., a maximum operating current) that is based on the resistance in the spool 114. In this situation, the useful energy output—the area under the curve shown in the current/time graph of FIG. 9*b*—is significantly less than the energy that would be output if the spool immediately reached its maximum operating current. The difference between the actual energy output and the maximum possible energy output is the lost energy shown in FIG. 9*b*.

Figure 9C:
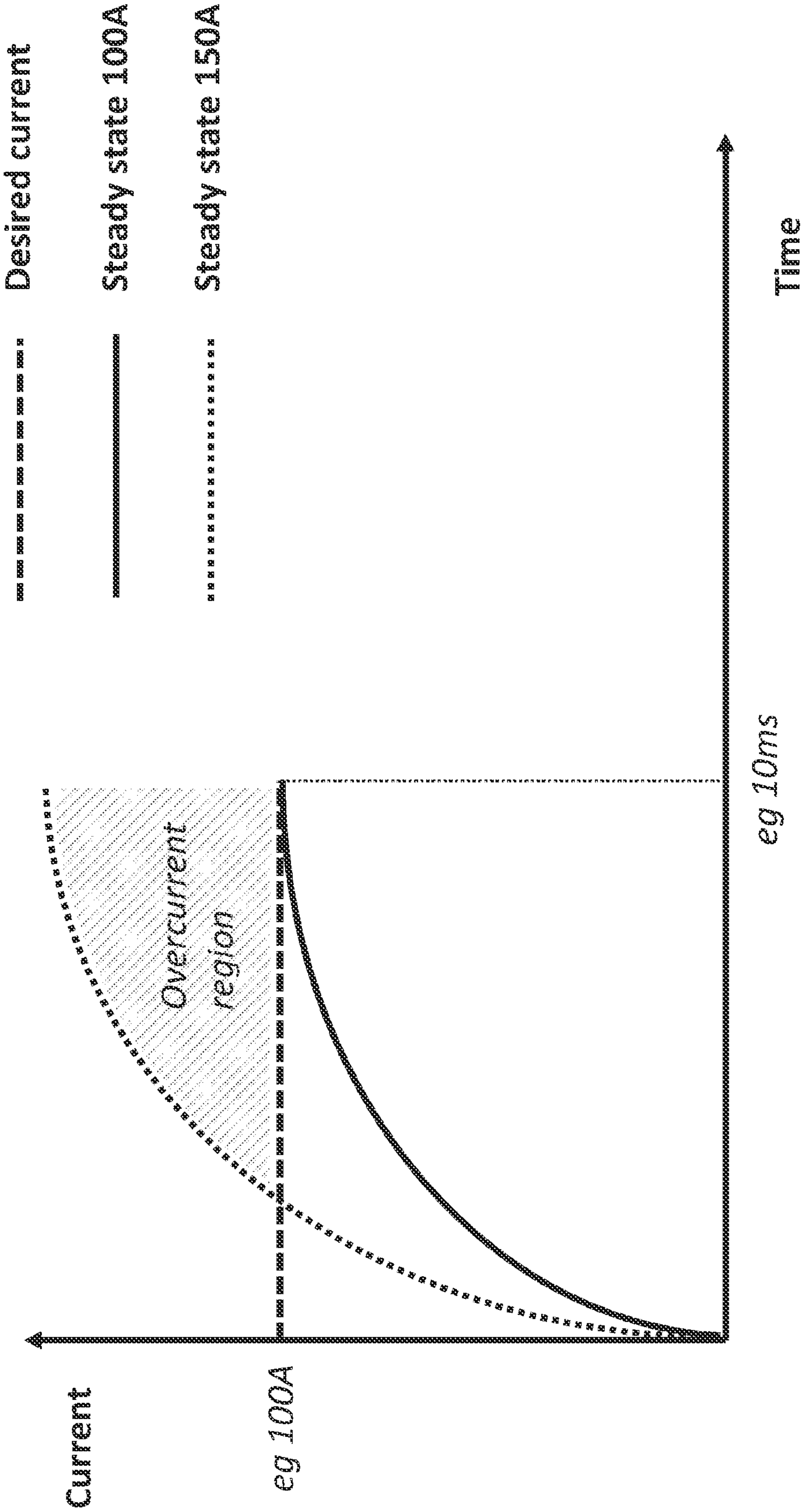

Therefore, as shown in FIG. 9*c*, the spool 114 may be provided with a high EMF such that the steady state current provided to the spool by the power source 2 exceeds the maximum operating current of the spool (and providing a high EMF in this manner can be considered to be the power source providing a current to the spool that is higher than the maximum operating current of the spool). The provision of such a high EMF results in the maximum operating current of the spool being reached rapidly. However, if such a high EMF is provided to the spool for an extended period of time, then the current in the spool might increase beyond the maximum operating current of the spool. This may cause damage in the spool.

Figure 9D:
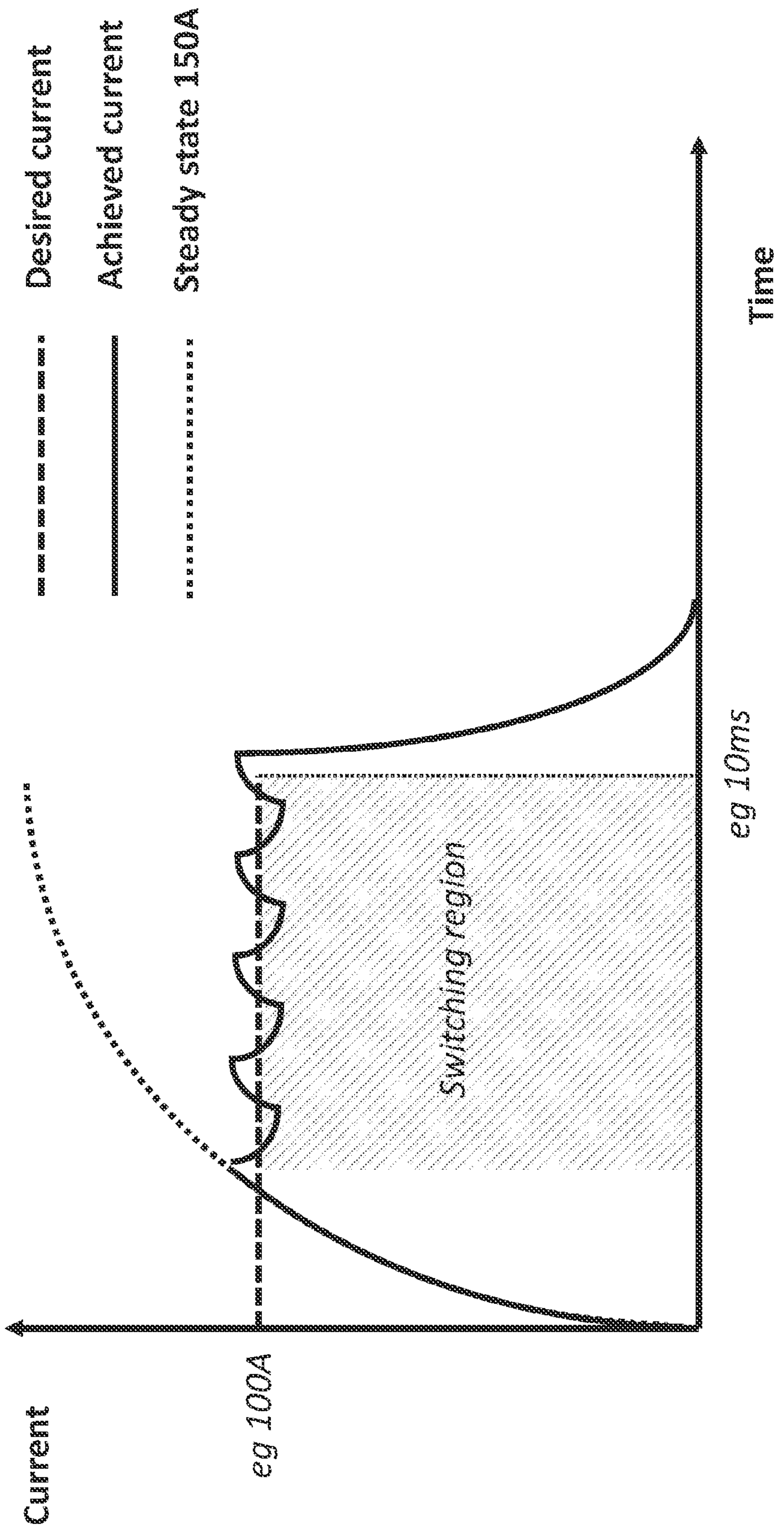

One method of mitigating over-current (where the current in the spool 114 exceeds the maximum operating current) is to introduce current monitoring and rapid spool switching—this method of operation is shown in FIG. 9*d*. Specifically, once the control electronics 4 detects that the current in the spool has exceeded the maximum operating current, the semiconductor is switched off so that the current starts to fall. Subsequently, once the control electronics 4 detects that the current in the spool has returned below the maximum operating current, the semiconductor is switched back on to increase the current in the spool. This process can be repeated to provide a current that oscillates about (or just below) the maximum operating current. By doing this, the spool 114 is tuned to draw the maximum safe current under the maximum load condition while preventing damage to the power source 2 or the spool in the no-load condition.

In practice, the control electronics 4 may be arranged to activate (e.g., switch on) a semiconductor when the current in the spool 114 is below a first value and to deactivate (e.g., switch off) the semiconductor when the current in the spool exceeds a second value.

It will be appreciated that the graph of FIG. 9*d* shows an exaggerated switching region, and in practice, using rapid switching it is possible to essentially hold the current at (or just below) the maximum operating current.

Furthermore, as explained with reference to FIG. 9*a*, the current in the spool 114 depends on the position of the strike assembly 126 and whether the strike assembly is imparting a force to the connector 112. Therefore, it is not possible to hold the spool at a constant current simply by providing a constant voltage and/or EMF to the spool. The intermittent provision of a high EMF by the power source 2 (which high EMF causes a high current to be provided to the spool) via a semiconductor enables the maximum operating current of the spool to be maintained throughout the impact, even in the presence of a back emf.

The method described with reference to FIG. 9*d* allows for the maximally effective drive of the spool without incurring the risk of overcurrent under load variance. In other words, this method greatly increases the amount of energy that can be provided to the spool 114 and so increases the maximum impact force that can be provided by the impactor 1. As well as this, by setting the current limit in software, the energy delivered to the spool and the stiffness during impaction (between stages 2 and 3) can be carefully controlled.

Alternatives and Modifications

It will be understood that the present invention has been described above purely by way of example, and modifications of detail can be made within the scope of the invention.

While the actuating mechanism 100 has been described above as using a spool 114 in order to provide a force to the body 104, other force providing mechanisms may be used. For example, a hydraulic, pneumatic, or chemical arrangement may be used to place a force on the body. In such arrangements, the feedback mechanism and the bi-directional operation of the impactor 1 still offer advantages over conventional products.

Furthermore, the separated strike assembly and connector still enable the provision of a high mass strike assembly and/or a low mass connector, which has beneficial properties such as reducing the fracture risk when the impactor is used for implanting.

In some embodiments, the connector 112 is affixed to, or an integral part of, the body 104. A (magnetic) force placed on the body can then directly impact an external object via the connector. In other words, the spool 114 may be used to place/effect a force on the body and this may be used to directly impart a force on an external object. In such embodiments, the connector may be considered to be a part of the strike assembly, which strike assembly also comprises the body, the distal striker 106, and the proximal striker 108.

Reference numerals appearing in the claims are by way of illustration only and shall have no limiting effect on the scope of the claims.

I claim:

1. An orthopedic impactor, comprising:

a housing enclosing:

a strike assembly;

a winding arranged to receive a current causing the winding to generate a magnetic field; and a connector configured to impart force to an object, wherein the housing encloses at least a portion of the connector; and wherein:

in a first operating mode, movement of the housing in a first direction causes the connector to move towards the object, wherein the strike assembly translates in a second direction being opposite the first direction, wherein the magnetic field generated by the winding, upon receiving of the current, causes the strike assembly to translate in the first direction impacting the connector, wherein, in the first operating mode, the current is provided to the winding causing substantially instantaneous translation of the strike assembly in the first direction; and in a second operating mode, movement of the housing in the second direction causes the connector to move away from the object in the second direction, wherein the strike assembly translates in the first direction, wherein the magnetic field generated by the winding, upon receiving of the current, causes the strike assembly to translate in the second direction impacting the connector, wherein, in the second operating mode, the current is provided to the winding causing an initial slow translation of the strike assembly in the first direction and, upon removal of the current from the winding, a substantially instantaneous translation of the strike assembly in the second direction.

2. The impactor of claim 1, wherein the object is configured to be implanted during the first operating mode, and the object is configured to be removed during the second operating mode.

3. The impactor of claim 1, wherein the connector is stationary.

4. The impactor of claim 3, wherein the connector is configured to transfer one or more forces from the strike assembly to the object.

5. The impactor of claim 1, further comprising a biasing mechanism configured to bias the strike assembly towards a resting position.

6. The impactor of claim 5, wherein the biasing mechanism comprises a spring, wherein the spring is configured to:

compress as the strike assembly is translated in the first direction in the first operating mode; and p1 extend as the strike assembly is translated in the second direction.

7. The impactor of claim 5, wherein, when the strike assembly is in the resting position, the winding does not receive the current.

8. The impactor of claim 1, wherein the strike assembly comprises a striker configured to impact the connector.

9. The impactor of claim 8, wherein the connector at least partially surrounds the striker and is configured to receive a force from the striker to impart a force to the object.

10. The impactor of claim 1, wherein the connector is configured to receive:

a first force from a proximal striker of the strike assembly; and a second force from a distal striker of the strike assembly.

11. The impactor of claim 1, wherein a body of the strike assembly comprises at least one of: a ferromagnetic material, iron, at least 70% iron, a permanent magnet configured to be moved by the magnetic field, and any combination thereof.

12. The impactor of claim 1, wherein the winding is configured to radially or axially surround a ferromagnetic body of the strike assembly.

13. The impactor of claim 1, further comprising a power source for supplying the current to the winding, wherein the power source includes at least one of: a battery, a capacitor, and any combination thereof.

14. The impactor of claim 1, further comprising an input for changing a parameter of a force impacting the connector, wherein the parameter including at least one of: a direction of the force, a magnitude of the force, a speed of application of the force, a frequency of application of the force, a duration of the force; an energy of an impact relating to the force, and any combination thereof.

15. The impactor of claim 1, further comprising an input for changing a parameter of the current received by the winding, wherein the parameter including at least one of: a direction of the current, a magnitude of the current, a duration of the current, a frequency of the current, a frequency of transmission of pulses of the current, and any combination thereof.

16. The impactor of claim 1, further comprising a sensor configured to measure at least one of: an impact a force impacting the connector, a stability of the object, a stability of an implant, an energy of an impact on the object, and any combination thereof.

17. The impactor of claim 1, further comprising control electronics communicatively coupled to at least one of: an input to the impactor, a power source of the impactor, and any combination thereof.

18. The impactor of claim 17, wherein the control electronics are configured to determine at least one of: a position of the strike assembly, a force of an impact based on the current and/or a voltage in the winding, and any combination thereof.

19. The impactor of claim 17, wherein the control electronics are configured to determine impactor use data, wherein the impactor use data includes at least one of the following: a bone quality, an implant stability, an impact force, a difference between an impact force and a desired force, an impact frequency, a user of the impactor, a hoop stress, and any combination thereof.

20. The impactor of claim 1, further comprising at least one of:

a bearing configured to support at least one of: the strike assembly and the connector;

a bearing holder configured to limit movement of the connector; and at least one of: a spacer and an end cap configured to limit movement of at least one of: the strike assembly and the connector.

* * * * *